United States Patent [19]

Walsh et al.

[11] Patent Number: 4,898,874
[45] Date of Patent: Feb. 6, 1990

[54] ACETIC ACID DERIVATIVES OF 3-ARYL-2,1-BENZISOXAZOLE AND ESTERS AND AMIDES THEREOF

[75] Inventors: David A. Walsh, Richmond; Ibrahim M. Uwaydah, Chesterfield, both of Va.

[73] Assignee: A. H. Robins Company, Inc., Richmond, Va.

[21] Appl. No.: 906,965

[22] Filed: Sep. 15, 1986

[51] Int. Cl.[4] .................. A61K 31/42; C07D 261/20
[52] U.S. Cl. ............................... 514/379; 514/233.8; 514/253; 514/321; 544/137; 544/368; 546/198; 548/241; 558/405; 562/460; 564/166
[58] Field of Search .................. 548/241; 514/379

[56] References Cited

U.S. PATENT DOCUMENTS 3,951,999  4/1976  Saunders et al. .................. 548/241
4,728,662  3/1988  Shutske et al. .................... 514/379

OTHER PUBLICATIONS

Campbell et al., Chemical Abstracts, No. 16157, vol. 62, (1965).
Zinic et al., J. Het. Chem., 14, p. 1225 (1977).
Earley et al., J. Pharm. Sci., 68, p. 845 (1979).
Loudon et al., J. Chem. Soc., p. 3092 (1962).
Saunder and Williams, J. Med. Chem., 1979, vol. 22, 1554–1558.
Dunwell and Evans, J. Med. Chem., 1977, vol. 20, 797–801.

Primary Examiner—Mukund J. Shah
Assistant Examiner—F. Beinhardt

[57] ABSTRACT

3-Aryl-2,1-benzisoxazole compounds having the formula:

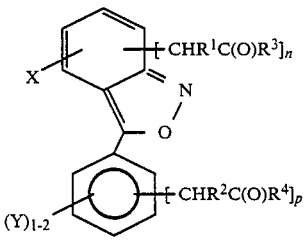

wherein
$R^1$ and $R^2$ are hydrogen or methyl;
$R^3$ and $R^4$ are hydroxyl, loweralkoxy, amino or —OM wherein M is a pharmaceutically acceptable cation;
X is hydrogen, halogen, loweralkyl or nitro;
Y is selected from hydrogen, halogen, loweralkyl, loweralkoxy, nitro or trifluoromethyl;
n and p are zero or one with the proviso that either n or p must be one are disclosed, having anti-inflammatory activity and novel intermediates in the preparation thereof.

66 Claims, No Drawings

ACETIC ACID DERIVATIVES OF 3-ARYL-2,1-BENZISOXAZOLE AND ESTERS AND AMIDES THEREOF

BACKGROUND OF THE INVENTION

1. Field of Invention

The present invention relates to novel acetic acid derivatives of 3-aryl-2,1-benzisoxazole, including esters, amides, and metal salts thereof, methods of preparation, pharmaceutical methods and compositions for treating living animals for inflammation therewith, and the novel acetonitrile intermediates for the preparation thereof.

2. Description of the Prior Art

Preparation of the 3-aryl-2,1-benzisoxazoleacetic acids and derivatives of the present invention has not previously been reported in the literature. A failed attempt to make a compound having the structure falling within the scope of the present invention, namely the compound structure:

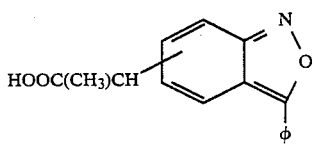

was reported in J. HETEROCYCLIC CHEM. 14, 1225 (1977).

Aryl benzoxazoleacetic acids having the formula:

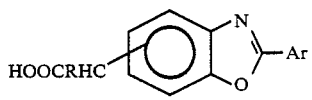

have been reported in J. MED. CHEM. 18, 53 (1975); 20 169 (1977) and 20, 797 (1977). In these references the oxygen and nitrogen are separated by the carbon bearing the aryl group whereas they are adjacent in the present invention.

Aryl-1,2-benzisoxazoleacetic acids having the formula:

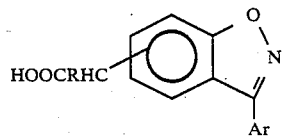

have been reported in J. MED. CHEM. 22, 1554 (1979).

In this reference the oxygen is adjacent to the phenyl moiety of benzoxazole ring, whereas in the present invention the nitrogen is adjacent.

Conversion of 2-aminobenzophenones to 3-aryl-2,1-benzisoxazoles; i.e., 3-arylanthranils, has long been known, C.A. 62, 16,157 (1965).

5-Carboxy-3-phenyl-2,1-benzisoxazole and its methyl ester are known, C.A. 77, 164,573e as is 6-carboxy-3-phenyl-2,1-benzisoxazole, C.A. 90, 186,909q.

2-Phenyl-6-benzoxazoleacetonitrile and its α-methyl derivative are known, C.A. 87, 62,486t. 2-Phenyl-5-benzoxazoleacetonitrile and its α-methyl derivative are known, C.A. 80, P70,798a; C.A. 81, P105,488r; C.A. 82, 118,774b and C.A. 85, P142,806w. These compounds are isomers only and not useful intermediates in preparation of compounds of Formula I.

SUMMARY OF THE INVENTION

The novel acetic acid derivatives of 3-aryl-2,1-benzisoxazole including esters and amides thereof of the present invention have the formula:

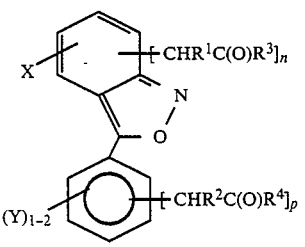

Formula I wherein;

$R^1$ and $R^2$ are selected from hydrogen or methyl;

$R^3$ and $R^4$ are selected from —OH, loweralkoxy, Am or —OM wherein Am is selected from —NH$_2$, —NH-loweralkyl, —N-(loweralkyl)$_2$, or a heterocyclic amine selected from 4-morpholinyl, 1-pyrrolidinyl, 1-piperidinyl, 1-piperazinyl and 4-substituted piperazin-1-yl, and M is a pharmaceutically acceptable cation;

X is selected from hydrogen, halogen, loweralkyl or nitro;

n and p are zero or one with the proviso that either n or p must be one or both n and p are one; and Y is selected from hydrogen, halogen, loweralkyl, loweralkoxy, nitro or trifluoromethyl with the further proviso that X and/or Y can be loweralkyl when only the 7-position of the benzisoxazole ring is substituted by a —CHR$^1$C(O)R$^3$ radical and the phenyl radical carries only a Y radical.

The novel chemical intermediates useful in preparation of compounds of Formula I have the formula:

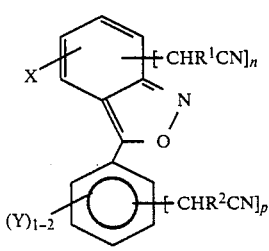

Formula II wherein;

$R^1$ and $R^2$ are hydrogen or methyl;

X is selected from hydrogen, halogen, loweralkyl or nitro;

n and p are zero or one with the proviso that either n or p must be one or both n and p are one; and Y is selected from hydrogen, halogen, loweralkyl, loweralkoxy, nitro or trifluoromethyl with the further proviso that X and/or Y can be loweralkyl when only the 7-position of the benzisoxazole ring is substituted by a

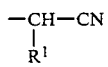

radical and the phenyl radical carries only a Y radical.

In the further definition of symbols and in the formulas hereof and where they appear elsewhere throughout this specification and in the claims, the terms have the following significance.

Pharmaceutically acceptable metal salts are formed when $R^3$ and/or $R^4$ are —OM as stated above and include compounds wherein M is $Na^+$, $K^+$, $Mg^{++}$, $Ca^{++}$, $Cu^{++}$, $Al^{+++}$, or $Zn^{++}$ and the like.

The term "4-substituted piperazine" refers to piperazine substituted in the 4-position by, for example, a blocking agent such as an acyl radical or by a loweralkyl radical or known radical which does not adversely affect the use of the compound as an antiinflammatory agent.

The term "loweralkyl" as used herein, unless otherwise specified, includes straight and branched chain radicals of up to eight carbons inclusive and is exemplified by such groups as methyl, ethyl, propyl, isopropyl, butyl, sec. butyl, tert-butyl, amyl, isoamyl, hexyl, heptyl and octyl radicals and the like. The term "loweralkoxy" has the formula -O-loweralkyl.

The terms "halo" or "halogen" as used herein includes fluorine, chlorine, bromine and iodine. Preferably, the halogen is chlorine or bromine.

The anti-inflammatory utility of the novel compounds of this invention was determined using the Evans Blue-Carrageenan Pleural Effusion Assay Method of Sancilio and Fishman in TOXICOL. APPL. PHARMAC. 26, 575–584 (1973), and a modification of the Adjuvant-Induced Arthritis Method of Walz, D. T. et al., J. PHARMAC. EXP. THER. 178, 223–231 (1971).

DETAILED DESCRIPTION OF THE INVENTION

The compounds of Formula I are prepared by an appropriate choice of reactions illustrated by equations in Chart I and II. Compounds of Formula I wherein X and/or Y are other than loweralkyl may be prepared via the procedure of Method B in Chart II for preparation of intermediates (II) followed by the procedure of Chart I. Compounds wherein X and/or Y are other than nitro, including loweralkyl, may be prepared by the procedure of Method A in Chart II followed by the procedure of Chart I with the same provisos as given under Formula I above. The proviso in the definitions of Formulas I and II, that X and/or Y can be loweralkyl when only the 7-position of the benzisoxazole ring is substituted by —$CHR^1C(O)R^3$ radical derives from the following limitations of the methods of preparation of the intermediates which conclusion can be drawn by one skilled in the art from the following:

(a) Method A allows preparation of compounds wherein X or Y is methyl, but it is limited to preparation of 7-benzisoxazoleacetonitriles;

(b) In Method B, any additional loweralkyl radicals would also undergo indiscriminant bromination, thus giving eventually a mixture of differently positioned acetonitrile side chains.

Certain 3-phenyl-2,1-benzisoxazole-5-acetamides may also be prepared by reactions illustrated in Chart III.

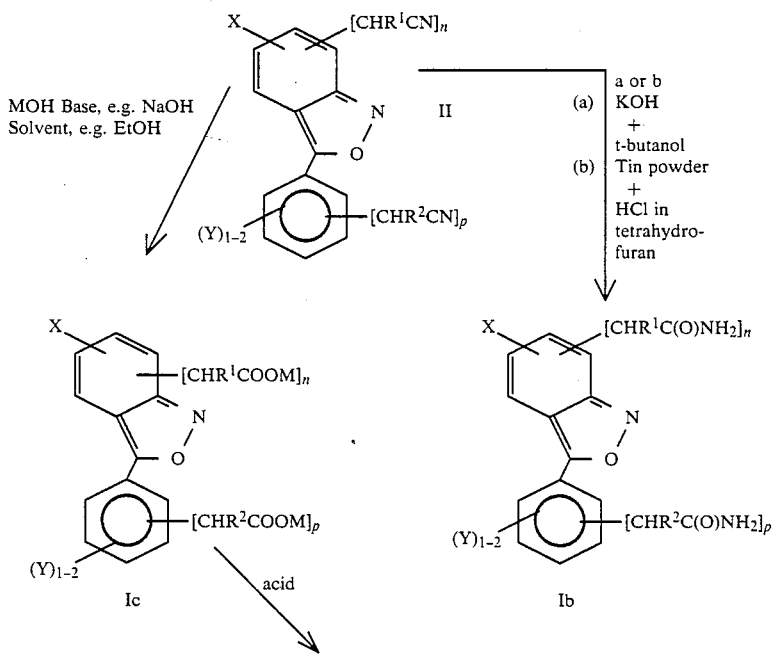

CHART I
Conversion of Acetonitrile* Intermediates to
Acetic Acid Derivatives of Formula I*

CHART I
Conversion of Acetonitrile* Intermediates to Acetic Acid Derivatives of Formula I*
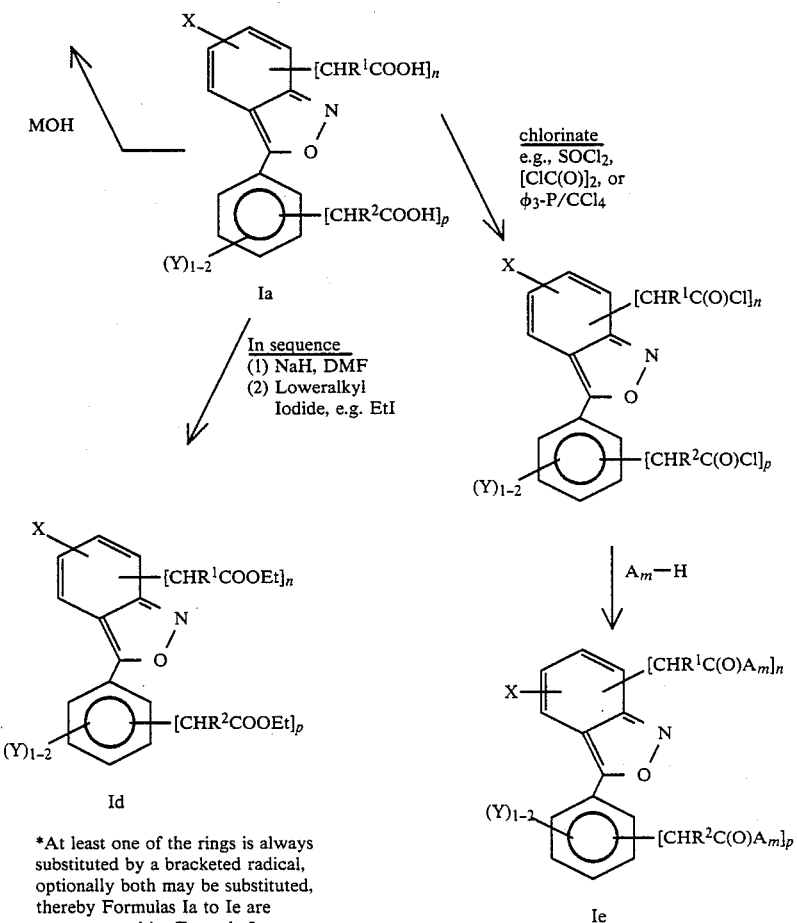
*At least one of the rings is always substituted by a bracketed radical, optionally both may be substituted, thereby Formulas Ia to Ie are emcompassed by Formula I.
CHART II
Preparation of Acetonitrile Intermediates
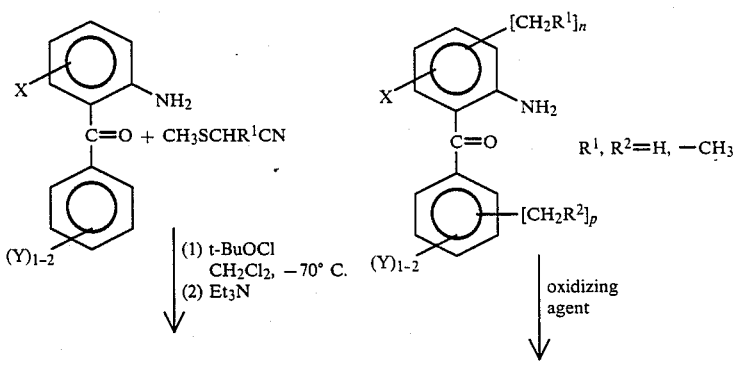

-continued
CHART II
Preparation of Acetonitrile Intermediates
METHOD A  
(X and/or Y other than NO$_2$)
METHOD B  
( X and/or Y other than loweralkyl)(a), (b)
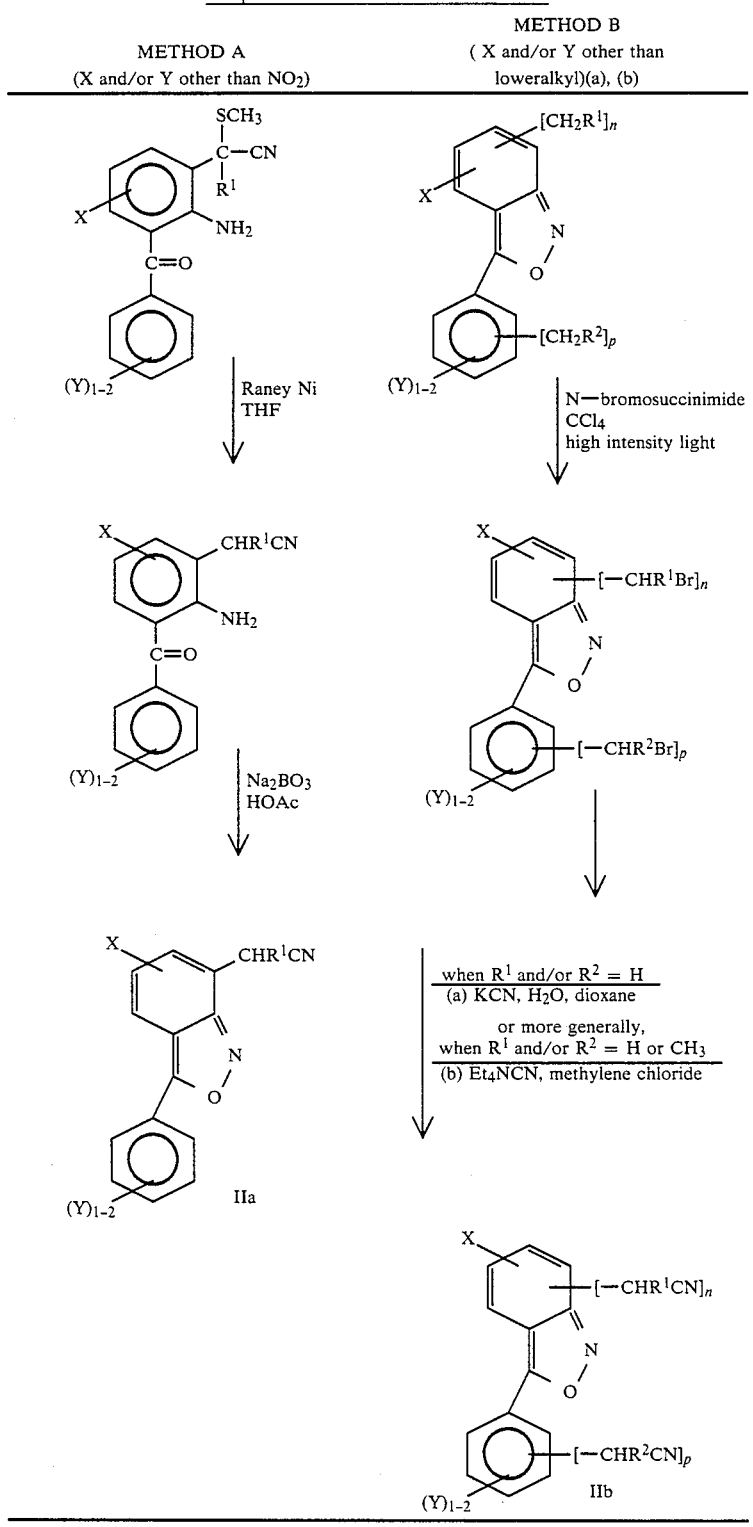
(a) At least one of the rings is always substituted by a bracketed radical; Optionally both may be substituted.
(b) X and/or Y cannot be loweralkyl in Method B.

CHART III
Independent Synthesis of Certain
3-Phenyl-2,1-benzisoxazole-5-acetamides*

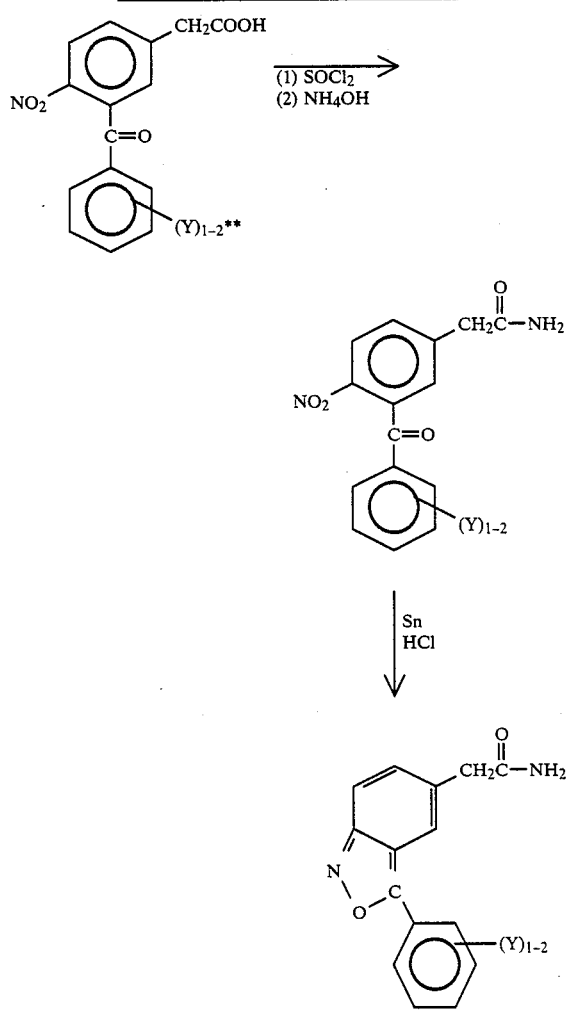

Footnotes to Chart III.
*See Intermediates 62 and 63 and Example 15 for 4-chlorophenyl derivative.
**Y is hydrogen, halogen, loweralkyl, loweralkoxy or trifluoromethyl.

Compounds of Formula I wherein p is zero have the formula:

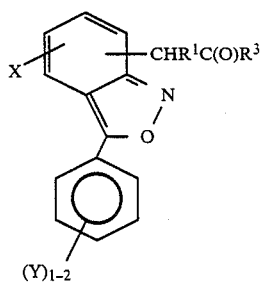

$I_x$ wherein;
$R^1$ is hydrogen or methyl;
$R^3$ is selected from OH, loweralkoxy, Am or —OM wherein Am is selected from —NH$_2$, —NH-loweralkyl, —N(loweralkyl)$_2$ or a heterocyclic amine selected from 1-pyrrolidinyl, 4-morpholinyl, 1-piperidinyl, 1-piperazinyl and 4-substituted piperazin-1-yl, and M is a pharmaceutically acceptable cation;
X is selected from hydrogen, halogen, loweralkyl or nitro; and
Y is selected from hydrogen, halogen, loweralkyl, loweralkoxy, nitro or trifluoromethyl with the proviso that X and/or Y can be loweralkyl only when the —CHR$^1$C(O)R$^3$ radical is in the 7-position.

Compounds of Formula I wherein n is zero have the formula:

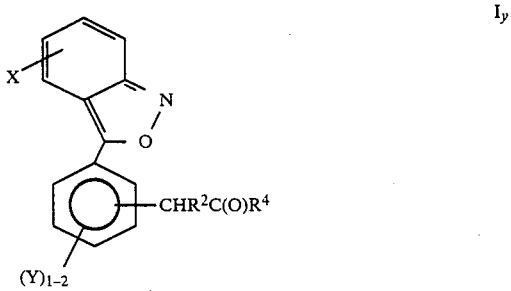

$I_y$ wherein;
$R^2$ is hydrogen or methyl;
$R^4$ is selected from —OH, loweralkoxy, Am or —OM wherein Am is selected from —NH$_2$, —NH-loweralkyl, —N(loweralkyl)$_2$ or a heterocyclic amine selected from 1-pyrrolidinyl, 4-morpholinyl, 1-piperidinyl, 1-piperazinyl or 4-substituted piperazin-1-yl, and M is a pharmaceutically acceptable cation;
X is selected from hydrogen, halogen or nitro, and
Y is selected from hydrogen, halogen, loweralkoxy, nitro or trifluoromethyl.

The process represented by Chart I is comprised of the following steps:
Step 1, reacting a compound having the formula

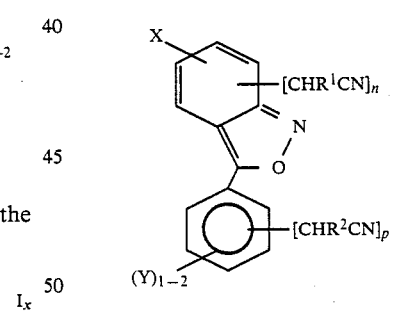

wherein X, Y, $R^1$, $R^2$, n and p are as defined under Formula I,
with (a) a hydrolyzing agent in a solvent medium favorable to hydrolysis and acidifying to give an acid compound having the formula:

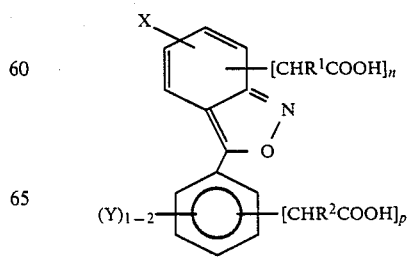

or (b) an amidating agent in an appropriate solvent to give a compound of the formula:

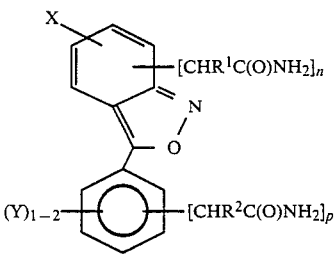

Step 2, esterifying an acid compound obtained in Step 1 by reacting with sodium hydride followed by loweralkyl iodide; e.g., ethyl iodide, to obtain an ester having the formula:

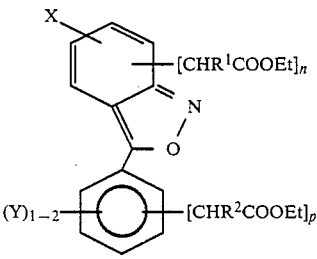

Step 3, halogenating an acid obtained in Step 1 to obtain an acid halide; e.g., acid chloride, compound having the formula:

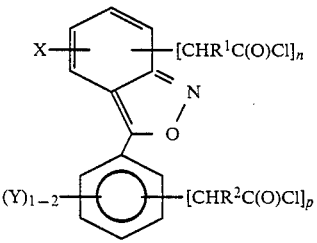

Step 4, reacting an acid halide; e.g., acid chloride, with an amine having the formula:

AmH wherein AmH is selected from ammonia, a monoalkyl amine, a diloweralkyl amine, or a heterocyclic amine selected from pyrrolidine, morpholine, piperidine, 4-phenyl-4-hydroxy-piperidine, piperazine or 4-substituted piperazine, e.g., 4-acetylpiperazine, to give a compound having the formula:

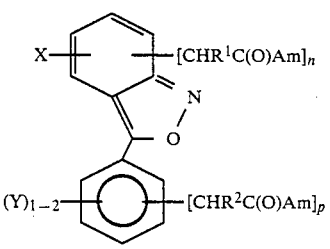

wherein X, Y, $R^1$, $R^2$, n, p and Am are as defined under Formula I.

Common metal salts; e.g., sodium and potassium salts, of the benzisoxazoleacetic acids are precursors to the acids as a result of alkaline hydrolysis of the benzisoxazoleacetonitriles, See Chart I. However, generally, it is advantageous because of ease of purification to convert to the acid form and reconvert back to the salt or to any of the metal salts given under the definition for pharmaceutically acceptable metal salts hereinabove. Such salts are prepared by reacting the purified acid with an appropriate salt-forming agent, illustratively, sodium hydroxide, potassium hydroxide, magnesium chloride and the like and precipitating the salt with an appropriate solvent pair.

The reaction conditions employed are more fully set forth hereinafter in the specific preparation of Intermediates and Examples. The preparation of Intermediates and Examples are not intended to be limiting, however.

INTERMEDIATE 1

3-(3-Methylphenyl)-2,1-benzisoxazole

A solution of 175 ml of 30% hydrogen peroxide and 350 ml of glacial acetic acid was heated on a steam bath for 1 hr and then cooled to 30° C. To the solution was added 31.6 g (0.15 mole) of 2-amino-3'-methylbenzophenone and the dark solution was let stand at ambient temperature over the weekend. The solution was poured into 3 liters of ice water and the mixture was extracted with three 300 ml portions of diethyl ether. The combined extracts were washed with three 300 ml portions of water, three 300 ml portions of saturated sodium bicarbonate solution, two 300 ml portions of water, and once with brine. The diethyl ether solution was dried over sodium sulfate and concentrated to give 28.0 g of oil as residue. This residue was chromatographed on 600 g of silica gel and the product was eluted with benzene-ligroin [1:1] solution. The product crystallized when scratched in the cold with petroleum ether. The gummy solid was recrystallized from 2-propanol by dissolving the solid at ambient temperature and cooling the solution in a dry ice-acetone bath to yield 15.6 g (50%) of solid. An analytical sample, m.p. 47°–48° C., was prepared from 2-propanol.

Analysis: Calculated for $C_{14}H_{11}NO$: C,80.36; H,5.30; N,6.69. Found: C,80.16; H,5.30; N,6.65.

INTERMEDIATE 2

3-[(3-Bromomethyl)phenyl]-2,1-benzisoxazole

A mixture of 14.9 g (0.071 mole) of 3-(3-methylphenyl)-2,1-benzisoxazole, 12.7 g (0.071 mole) of N-bromosuccinimide, 0.1 g of dibenzoylperoxide and 250 ml of carbon tetrachloride was heated at reflux under illumination of a floodlamp for 2 hr. The mixture was filtered and the filtrate was washed once with a saturated sodium bicarbonate solution, dried over sodium sulfate and concentrated to give a tan solid as residue. An NMR analysis of the solid showed that it was a mixture consisting of 22% of starting methyl compound, 63% of monobromo compound and 15% of dibromo compound. A portion was recrystallized from ethyl acetate to give an analytical sample of the title compound, m.p. 137°–139° C., with decomposition.

Analysis: Calculated for $C_{14}H_{10}BrNO$: C,58.36; H,3.50; N,4.86. Found: C,58.29; H,3.45; N,4.94.

INTERMEDIATE 3

3-(2,1-Benzisoxazol-3-yl)benzeneacetonitrile

A mixture of 19.5 g (0.68 mole) of crude (63% pure by NMR) 3-[(3-bromomethyl)phenyl]-2,1-benzisoxazole, 19.5 g (0.30 mole) of potassium cyanide, 200 ml of dioxane and 125 ml of water was heated at reflux under a nitrogen atmosphere for 4 hr. The mixture was cooled and diluted with 300 ml of methylene chloride. The layers were separated and the organic layer was washed twice with water (emulsion) and once with brine, dried over sodium sulfate and concentrated to give an oil as residue which gradually solidified. The solid was chromatographed on 300 g of silica gel to yield 6.2 g (62%) of off-white needles, m.p. 122°–123.5° C. (after recrystallization from 2-propanol).

Analysis: Calculated for $C_{15}H_{10}N_2O$: C,76.91; H,4.30; N,11.96. Found: C,76.66; H,4.29; N,11.92.

INTERMEDIATE 4

3-[4-(Bromomethyl)phenyl]-2,1-benzisoxazole

A mixture of 14.9 g (0.071 mole) of 3-(4'-methylphenyl)-2,1-benzisoxazole, 12.7 g (0.071 mole) of N-bromosuccinimide, 0.1 g of dibenzoyl peroxide and 200 ml of carbon tetrachloride was heated at reflux under illumination by a flood lamp for 20 hr. The mixture was filtered while hot and the filtrate was washed twice with 5% aqueous sodium hydroxide, dried over sodium sulfate and concentrated. The residue was dissolved in acetonitrile and filtered to remove insoluble material. The filtrate was concentrated and the residue was recrystallized twice from ethanol and once from 2-propanol (charcoal) to yield 12.1 g (59%) of solid, m.p. 146°–147° C. with decomposition.

Analysis: Calculated for $C_{14}H_{10}BrNO$: C,58.36; H,3.50; N,4.86. Found: C,58.44; H,3.50; N,4.96.

INTERMEDIATE 5

4-(2,1-Benzisoxazol-3-yl)benzeneacetonitrile

A mixture of 11.1 g (0.039 mole) of 3-[4-(bromoethyl)phenyl]-2,1-benzisoxazole, 13.0 g (0.2 mole) of potassium cyanide, 55 ml of water and 80 ml of dioxane was heated at reflux under a nitrogen atmosphere for 2 hrs. The mixture was cooled, 200 ml of methylene chloride was added and the layers were separated. The organic layer was washed twice with water, dried over sodium sulfate and concentrated to give a gummy solid as residue. The residue was chromatographed on 150 g of silica gel and the product was eluted with 10% methanol in benzene to yield 4.4 g (48%) of solid, m.p. 118°–121° C. (after recrystallization from 2-propanol, charcoal).

Analysis: Calculated for $C_{15}H_{10}N_2O$: C,76.91; H,4.30; N,11.96. Found: C,76.73; H,4.22; N,12.09.

INTERMEDIATE 6

3-(4-Ethylphenyl)-2,1-benzisoxazole (2-Aminophenyl) (4-ethylphenyl)methanone, 60 g, (0.27 mole) was dissolved in 700 ml of 3% peracetic acid (prepared by warming a mixture of 500 ml of glacial acetic acid and 200 ml of 30% hydrogen peroxide on a steam bath for ½ hr, followed by cooling to 25° C.). The solution was allowed to stand for 60 hr, then poured into two liters of water. The mixture was extracted with methylene chloride and the organic extracts were diluted with ethyl acetate and extracted with dilute sodium hydroxide. The organic phase was then concentrated and the residue was chromatographed on silica gel, eluting with benzene. The product-containing benzene fractions were concentrated and the residue was distilled. The fraction boiling at 131° C./0.02 mmHg was collected and recrystallized from isopropanol to give 33.2 g (55%) of pale yellow crystals, m.p. 42.0°–42.5° C.

Analysis: Calculated for $C_{15}H_{13}NO$: C,80.69; H,5.87; N,6.27. Found: C,80.48; H,5.83; N,6.24.

INTERMEDIATE 7

3-[4-(1-Bromoethyl)phenyl]-2,1-benzisoxazole

A solution of 24.5 g (0.11 mole) of 3-(4-ethylphenyl)-2,1-benzisoxazole in 330 ml of carbon tetrachloride was heated to reflux and treated with 19.6 g (0.11 mole) of N-bromosuccinimide and 10 mg of benzoyl peroxide. The mixture was maintained at reflux by illumination with a floodlamp for 20 min, at which time all insoluble material was floating. The mixture was cooled and filtered. The filtrate was washed with dilute sodium bicarbonate solution and the organic fraction was concentrated to a yellow solid. The solid was recrystallized from 200 ml of isopropanol to give 29.0 g (87%) of yellow crystals, m.p. 105.5°–8.0° C.

Analysis: Calculated for $C_{15}H_{12}BrNO$: C,59.62; H,4.00; N,4.64. Found: C,59.87; H,4.01; N,4.75.

INTERMEDIATE 8

5-Methyl-3-phenyl-2,1-benzisoxazole

A solution of 31.6 g (0.15 mole) of 5-methyl-2-aminobenzophenone, 350 ml of glacial acetic acid and 17 ml of 30% hydrogen peroxide was let stand at ambient temperature for 72 hr. The solution was poured into 2.5 liters of water. The mixture was let stand at ambient temperature for several days until the residue became crystalline. The solid was collected by filtration, dried, and chromatographed on 250 g silica gel to give 12.5 g (40%) of pale yellow solid, m.p. 64°–66° C. (after recrystallization from 2-propanol).

Analysis: Calculated for $C_{14}H_{11}NO$: C,80.36; H,5.30; N,6.69. Found: C,80.15; H,5.27; N,6.66.

INTERMEDIATE 9

5-(Bromomethyl)-3-phenyl-2,1-benzisoxazole

A mixture of 11.7 g (0.05 g mole) of 5-methyl-3-phenyl-2,1-benzisoxazole, 10.0 g (0.056 mole) of N-bromosuccinimide and 0.1 g of dibenzoylperoxide in 200 ml of carbon tetrachloride was heated at reflux under illumination by a flood lamp for 2.5 hr. The mixture was filtered and the filtrate was washed with 5% sodium hydroxide, dried over sodium sulfate and concentrated to give a solid as residue. This solid was recrystallized twice from 2-propanol to yield 9.5 g (59%) of crystals, m.p. 130° C. (with decomposition).

Analysis: Calculated for $C_{14}H_{10}BrNO$: C,58.36; H,3.50; N,4.86. Found: C,58.77; H,3.52; N,4.92.

INTERMEDIATE 10

3-Phenyl-2,1-benzisoxazole-5-acetonitrile

A mixture of 9.1 g (0.032 mole) of 5-(bromomethyl)-3-phenyl-2,1-benzisoxazole, 9.8 g (0.15 mole) of potassium cyanide, 50 ml of water and 80 ml of dioxane was heated at reflux under nitrogen for 2.5 hr. The solution was cooled and diluted with 200 ml of methylene chloride. The layers were separated and the organic layer was washed twice with water (emulsion), dried over sodium sulfate and concentrated to give 8.6 g of a dark solid as residue. The solid was chromatographed on 180 g of silica gel eluting with 2% acetone in benzene and 5.8 g (80%) of solid was obtained from the eluant. An analytical sample, m.p. 107°–109° C. was prepared by recrystallizing with 2-propanol.

Analysis: Calculated for $C_{15}H_{10}N_2O$: C,76.91; H,4.30; N,11.96. Found: C,77.04; H,4.29; N,12.09.

INTERMEDIATE 11

5-Ethyl-3-phenyl-2,1-benzisoxazole

This compound was prepared by the procedure used to synthesize the compound of Intermediate 6. A combination of 63.0 g (0.28 mole) of 2-amino-5-ethylbenzophenone and 700 ml of 3% peracetic acid gave, after two recrystallizations from isopropanol and then isopropanol-isopropyl ether, 13.0 g (21%) of bright yellow blades, m.p. 57.0°–59.0° C.

Analysis: Calculated for $C_{15}H_{13}NO$: C,80.69; H,5.87; N,6.27. Found: C,80.63; H,5.84; N,6.27.

INTERMEIDATE 12

5-(1-Bromoethyl)-3-phenyl-2,1-benzisoxazole

A mixture of 15.4 g (0.069 mole) of 5-ethyl-3-phenyl-2,1-benzisoxazole, 12.4 g (0.0697 mole) of N-bromosuccinimide and 0.3 g of dibenzoyl peroxide in 300 ml of carbon tetrachloride was heated at reflux under floodlight illumination and an argon atmosphere for one hr and then filtered while still hot. The filtrate was concentrated under reduced pressure to give 22.0 g of a semi-solid residue (NMR indicated 80% product). A sample of this semi-solid was triturated with 3 ml of methylene chloride and filtered. The solid filter cake was recrystallized from ethyl ether to give yellow solid, m.p. 118°–119° C. (with decomposition).

Analysis: Calculated for $C_{15}H_{12}BrNO$: C,59.62; H,4.00; N,4.64. Found: C,59.55; H,3.98; N,4.58.

INTERMEDIATE 13

α-Methyl-3-phenyl-2,1-benzisoxazole-5-acetonitrile

A solution of 7.6 g (0.0486 mole) of tetraethylammonium cyanide in 100 ml of methylene chloride was stirred and heated at reflux under an argon atmosphere. To this solution was added a solution of 14.1 g (0.0397 mole) of crude 5-(1-bromoethyl)-3-phenyl-2,1-benzisoxazole in 60 ml of methylene chloride. The reaction mixture was heated at reflux for 5 hr and then concentrated under reduced pressure to give a dark semi-solid residue. The residue was extracted with 1.5 liter of ethyl ether (heating on a steam bath) and the solid was removed by filtration. The filtrate was evaporated under reduced pressure to give 6.2 g of a brown oily residue. A 1.0 g sample of this residue was purified by chromatography (3½×60 cm glass column; 90 g of silica gel; benzene). Fractions containing the title compound were combined and concentrated under reduced pressure to give an oily residue. The residue was crystallized from benzene-petroleum ether (30°–60° C.) to give 0.4 g (26%) of yellow solid, m.p. 92°–95° C.

Analysis: Calculated for $C_{16}H_{12}N_2O$: C,77.40; H,4.87; N,11.28. Found: C,77.23; H,4.91; N,11.12.

INTERMEDIATE 14

6-Methyl-3-phenyl-2,1-benzisoxazole

A solution of 31.6 g (0.15 mole) of 4-methyl-2-aminobenzophenone in 350 ml of glacial acetic acid and 175 ml of 30% hydrogen peroxide was let stand at ambient temperature for 72 hr. The solution was poured into 3 liters of water and a solid gradually crystallized. The solid was collected by filtration, washed with water and recrystallized from 2-propanol. The precipitate was slurried in 200 ml of carbon tetrachloride and filtered. The filtrate was concentrated to yield 10.5 g (35%) of title compound, m.p. 77.78° C. after recrystallization from 2-propanol.

Analysis: Calculated for $C_{14}H_{11}NO$: C,80.36; H,5.30; N,6.69. Found: C,80.46; H,5.28; N,6.65.

INTERMEDIATE 15

6-(Bromomethyl)-3-phenyl-2,1-benzisoxazole

A mixture of 13.3 g (0.064 mole) of 6-methyl-3-phenyl-2,1-benzisoxazole, 11.3 g (0.064 mole) of N-bromosuccinimide, 0.1 g of dibenzoylperoxide and 225 ml of carbon tetrachloride was heated at reflux under illumination by a flood lamp for 2.5 hr. The mixture was filtered and the filtrate was washed with 100 ml of 5% sodium bicarbonate, dried over sodium sulfate, and concentrated to give a solid as residue. The solid was recrystallized from 2-propanol to give 12.9 g (71%) predominantly the title compound as a tan solid. A reference sample, m.p. 127°–128° C. was recrystallized thrice from 2-propanol, but a satisfactory analysis could not be obtained. A TLC of the solid showed one spot and the $H^1$ and $C^{13}$ NMR and mass spectrum were consistent with the assigned structure.

Analysis: Calculated for $C_{14}H_{10}BrNO$: C,58.36; H,3.50; N,4.86. Found: C,57.45; H,3.41; N,4.81.

INTERMEDIATE 16

3-Phenyl-2,1-benzisoxazole-6-acetonitrile

A mixture of 10.9 g (0.038 mole) of slightly impure 6-(bromomethyl)-3-phenyl-2,1-benzisoxazole, 9.8 g (0.15 mole) of potassium cyanide, 80 ml of dioxane, and 50 ml of water was heated at reflux under a nitrogen atmosphere for 2.5 hr. The mixture was diluted with 200 ml of methylene chloride and the layers were separated. The organic layer was washed twice with water, once with brine, and dried over sodium sulfate, and concentrated to give 7.5 g of gray solid as residue. The solid was chromatographed on 150 g of silica gel and the title compound was eluted with 1% methanol in benzene to yield 3.3 g (37%) of product, m.p. 148°–155° C.

Analysis: Calculated for $C_{15}H_{10}N_2O$: C,76.91; H,4.30; N,11.96. Found: C,77.05; H,4.27; N,12.09.

INTERMEDIATE 17

6-Ethyl-3-phenyl-2,1-benzisoxazole

A solution of 300 ml of 30% hydrogen peroxide in 700 ml of glacial acetic acid was heated on a steam bath for 1 hr. To the cooled solution was added a solution of 64.0 g (0.284 mole) of (2-amino-4-ethylphenyl)phenylmethanone in 150 ml of glacial acetic acid. The dark reaction mixture was heated at 50°–70° C. for 0.5 hr, poured into 3 liters of ice water and let stand at ambient temperature overnight. The reaction mixture was extracted with six 200 ml portions of carbon tetrachloride. The combined carbon tetrachloride extracts were washed with three 200 ml portions of water and dried over magnesium sulfate. The solvent was concentrated under reduced pressure to 200 ml, treated with charcoal and filtered. The filtrate was evaporated under reduced pressure to give a dark oil as residue. A 9.0 g sample was purified by chromatography (3.5×60 cm glass column; 175 g of silica gel; benzene). Fractions containing the title compound were combined and the solvent evaporated under reduced pressure to give 6.2 g (57%) of oil. The oil was dissolved in 2-propanol and cooled to dry ice acetone temperatures to give light yellow crystals, m.p. 41°-43° C.

Analysis: Calculated for $C_{15}H_{13}NO$: C,80.69; H,5.87; N,6.27. Found: C,80.51; H,5.87; N,6.24.

INTERMEDIATE 18

6-(1-Bromoethyl)-3-phenyl-2,1-benzisoxazole

A mixture of 1.9 g (0.0085 mole) of 6-ethyl-3-phenyl-2,1-benzisoxazole, 1.5 g (0.0087 mole) of N-bromosuccinimide and a few crystals of dibenzoyl peroxide in 100 ml of carbon tetrachloride was heated at reflux for 2 hr under floodlight illumination and under an argon atmosphere. The cooled reaction mixture was filtered, and the filtrate was washed twice with 100 ml portions of 10% sodium bicarbonate solution, once with water (100 ml) and dried over sodium sulfate. The sodium sulfate was removed by filtration and the filtrate was concentrated to a dark brown oil which solidified upon standing. The solid was purified by chromatography (3.5×60 cm glass column; 180 g of silica gel; benzene). Fractions containing the title compound were combined and the solvent was evaporated under reduced pressure to give a viscous oil which solidified upon standing. The solid was recrystallized from diethyl ether-petroleum ether (30°-60° C.) to give 1.7 g (65%) of mustard yellow crystals, m.p. 99°-102° C.

Analysis: Calculated for $C_{15}H_{12}BrNO$: C,59.64; H,4.00; N,4.64. Found: C,59.58; H,4.01; N,4.59.

INTERMEDIATE 19

α-Methyl-3-phenyl-2,1-benzisoxazole-6-acetonitrile

A solution of 9.8 g (0.062 mole) of tetraethylammonium cyanide in 100 ml of methylene chloride was heated at reflux under an argon atmosphere. To this solution was added a solution of 16.0 g (0.052 mole) of 6-(1-bromoethyl)-3-phenyl-2,1-benzisoxazole in 80 ml of methylene chloride. The reaction mixture was heated at reflux for 4 hr. The solvent was evaporated under reduced pressure and the dark semi-solid pot residue was triturated successively with 1.3 liters of diethyl ether and with 800 ml of benzene and filtered. The combined filtrates were concentrated under reduced pressure to give 10.5 g of a dark-brown, viscous oil as residue.

The oil was purified by chromatography (4.5×105 cm glass column; 480 g of silica gel; benzene). Fractions containing the title compound were combined, and the solvent was evaporated under reduced pressure to give 7.3 g (56%) of a viscous oil which solidified upon standing. A sample of the solid was recrystallized twice from benzene-petroleum ether to give an off-white solid. m.p., 129°-133° C.

Analysis: Calculated for $C_{16}H_{12}N_2O$: C,77.40; H,4.87; N,11.28. Found: C,77.43; H,4.83; N,11.20.

INTERMEDIATE 20

7-Methyl-3-phenyl-2,1-benzisoxazole

A solution of 8.4 g (0.04 mole) of 3-methyl-2-aminobenzophenone, 150 ml of acetic acid and 40 ml of 30% hydrogen peroxide was allowed to stand at ambient temperature for 3 days and the resulting solution was poured into 800 ml of ice-water mixture. The solid which precipitated was collected by filtration, washed with water and dried. This solid was recrystallized twice from isopropanol to yield 4.1 g (49%) of tan crystals, m.p. 73°-75° C.

Analysis: Calculated for $C_{14}H_{11}NO$: C,80.36; H,5.30; N,6.69. Found: C,80.39; H,5.51; H,6.69.

INTERMEDIATE 21

7-Bromomethyl-3-phenyl-2,1-benzisoxazole

A solution of 23.5 g (0.112 mole) of 7-methyl-3-phenyl-2,1-benzisoxazole in 400 ml of carbon tetrachloride was treated with 20.0 g (0.112 mole) of N-bromosuccinimide and the mixture was heated at reflux with a white light lamp until all solid floated in the solvent. The mixture was filtered and the filtrate deposited a 15 g crop of reasonably pure product. This 15 g of material was dissolved in methylene chloride and washed with diluted sodium hydroxide to remove succinimide. The organic solution was concentrated and the residue was crystallized from isopropanol to give 25.2 g (77%) of yellow needles, m.p. 125.0°-125.5° C.

Analysis: Calculated for $C_{14}H_{10}BrNO$: C,58.36; H,3.50; N,4.86. Found: C,58.48; H,3.45; N,4.93.

INTERMEDIATE 22

3-Phenyl-2,1-benzisoxazol-7-acetonitrile

A mixture of 17.3 g (0.06 mole) of 7-bromomethyl-3-phenyl-2,1-benzisoxazole, 17 g of potassium cyanide, 80 ml of water and 120 ml of dioxane was heated at reflux under a nitrogen atmosphere for 2 hr. The mixture was then cooled and diluted with 300 ml of methylene chloride. The organic layer was separated, washed with water and dried over magnesium sulfate. The solvents were removed under vacuum and the residue was crystallized twice from absolute ethanol to give 10.3 g (74%) of yellow crystals, m.p. 125°-138° C.

Analysis: Calculated for $C_{15}H_{10}N_2O$: C,76.91; H,4.30; N,11.96. Found: C,77.21; H,4.36; N,11.92.

INTERMEDIATE 23

7-Ethyl-3-phenyl-2,1-benzisoxazole

A solution of 7.5 g (0.033 mole) of 3-ethyl-2-aminobenzophenone in 150 ml of acetic acid and 40 ml of 30% hydrogen peroxide was let stand at ambient temperature for 72 hr. The solution was poured into ice water and a solid gradually crystallized. The solid was collected by filtration, washed with water and dried. The solid was then slurried with 20 ml of carbon tetrachloride and the mixture was filtered.

The filtrate was concentrated to give an oil which gradually crystallized. The solid was recrystallized from 30 ml of 2-propanol (dry ice-acetone temperatures) to give 3.0 g (40%) of pale yellow solid, m.p. 36°-38° C.

Analysis: Calculated for $C_{15}H_{13}NO$: C,80.69; H,5.87; N,6.23. Found: C,80.41; H,5.81; N,6.26.

INTERMEDIATE 24

7-(1-Bromoethyl)-3-phenyl-2,1-benzisoxazole

To a solution of 12.2 g (0.054 mole) of 7-ethyl-3-phenyl-2,1-benzisoxazole in 60 ml of carbon tetrachloride was added 10.5 g (0.059 mole) of N-bromosuccinimide and 0.1 g of dibenzoylperoxide. The stirred reaction mixture was heated at reflux under flood light illumination and an argon atmosphere for 2.5 hr. The cooled reaction mixture was filtered and the filter cake was washed with 40 ml of carbon tetrachloride. The combined filtrates were washed with three 100 ml portions of 10% sodium bicarbonate, twice with 100 ml portions of water and dried over sodium sulfate. The sodium sulfate was removed by filtration, the filtrate was treated with charcoal and filtered. The filtrate was concentrated to give 16.2 g (98%) of slightly impure title compound as a light brown oil that solidified upon standing. A sample was recrystallized from diethyl ether-petroleum ether (30°–60° C.) to give yellow crystals, m.p. 73°–77° C.

Analysis: Calculated for $C_{15}H_{12}BrNO$: C,59.62; H,4.00; N,4.64. Found: C,59.24; H,3.95; N,4.64.

INTERMEDIATE 25

α-Methyl-3-phenyl-2,1-benzisoxazole-7-acetonitrile

A solution of 8.9 g (0.0569 mole) of tetraethylammonium cyanide in 80 ml of methylene chloride was stirred and heated at reflux under an argon atmosphere. To this solution was added a solution of 14.5 g (0.048 mole) of 7-(1-bromoethyl)-3-phenyl-2,1-benzisoxazole in 60 ml of methylene chloride. The reaction mixture was heated at reflux for 19 hr and then concentrated under reduced pressure to give a semi-solid residue. The residue was triturated with 600 ml of ethyl ether and filtered. The filter cake was washed with 200 ml of ethyl ether. The combined filtrates were washed with three 200 ml portions of water and dried over magnesium sulfate. The solvents were concentrated under reduced pressure to 200 ml, treated with charcoal and filtered. The filtrate was evaporated under reduced pressure to give an oily residue which solidified upon standing. The solid was recrystallized from benzene-petroleum ether (30°–60° C.) to give 5.2 g (44%) of yellow crystals.[1] A sample was further purified by chromatography (3.5×60 cm glass comumn; 100 g of silica gel; benzene). Fractions containing the title compound were combined and concentrated under reduced pressure to give a solid. The solid was recrystallized from benzene-petroleum ether (30°–60° C.) to give an off-white solid, m.p. 109°–112° C.

[1] An additional 3.5 g of title compound was recovered from the filtrate by chromarography. Total yield was 8.7 g (73%).

Analysis: Calculated for $C_{16}H_{12}O$: C,77.40; H,4.87; N,11.28. Found: C,77.37; H,4.90; N,11.18.

INTERMEDIATE 26

3-(4-Fluorophenyl)-7-methyl-2,1-benzisoxazole

A solution of 250 ml of 30% hydrogen peroxide and 500 ml of acetic acid was heated on a steam bath for 1 hr, cooled, and treated with 45.8 g (0.2 mole) of 2-amino-3-methylphenyl)-(4-fluorophenyl)methanone. An additional 350 ml of acetic acid was added and the solution was heated at 60°–70° C. for 4 hr. The solution was poured into 2.5 liters of ice water and the resulting solid was collected by filtration, washed with water, dried, and recrystallized from 2-propanol to yield 9.8 g (22%) of tan solid, m.p. 134°–136° C.

Analysis: Calculated for $C_{14}H_{10}FNO$: C,74.00; H,4.44; N,6.16. Found: C,73.67; H,4.38; N,6.14.

INTERMEDIATE 27

7-(Bromomethyl)-3-(4-fluorophenyl)-2,1-benzisoxazole

A mixture of 9.7 g (0.0427 mole) of 3-(4-fluorophenyl)-7-methyl-2,1-benzisoxazole, 7.7 g (0.0431 mole) of N-bromosuccinimide and 0.2 g of dibenzoyl peroxide in 300 ml of carbon tetrachloride was heated at reflux under floodlight illumination and under an argon atmosphere for 3.5 hr. The cooled reaction mixture was filtered and the filtrate was concentrated under reduced pressure to give 10.4 g of solid. The solid was recrystallized twice from 2-propanol to give 9.0 g (69%) of light-yellow, fluffy needles, m.p. 145°–148° C.

Analysis: Calculated for $C_{14}H_9BrFNO$: C,54.93; H,2.96; N,4.58. Found: C,55.31; H,3.00; N,4.49.

INTERMEDIATE 28

3-(4-Fluorophenyl)-2,1-benzisoxazole-7-acetonitrile

A solution of 5.2 g (0.0333 mole) of tetraethylammonium cyanide in 100 ml of methylene chloride was stirred and heated at reflux under an argon atmosphere. To this solution was added a solution of 8.5 g (0.0278 mole) of 7-(bromomethyl)-3-(4-fluorophenyl)-2,1-benzisoxazole in 150 ml of methylene chloride. The reaction mixture was heated at reflux for 2 hr. The solvent was evaporated under reduced pressure and the dark pot residue was triturated with 800 ml of diethyl ether and filtered. The filtrate was concentrated under reduced pressure to give 5.1 g of a solid. The solid was dissolved in 100 ml of methylene chloride, treated with charcoal and filtered. The filtrate was evaporated under reduced pressure to give a solid as residue. The solid was recrystallized once from cyclohexane and twice from benzene to yield 3.8 g (54%) of yellow solid, m.p. 158°–160° C.

Analysis: Calculated for $C_{15}H_9FN_2O$: C,71.42; H,3.60; N,11.11. Found: C,71.30; H,3.61; N,10.80.

INTERMEDIATE 29

3-(4-Chlorophenyl)-7-methyl-2,1-benzisoxazole

A solution of 49 g (0.2 mole) of (2-amino-3-methylphenyl)(4-chlorophenyl)methanone, 1 liter of glacial acetic acid and 200 ml of 30% hydrogen peroxide was let stand at ambient temperature over the weekend. The mixture was heated on a steam bath for 1 hr and poured into 2.5 liters of ice water. The solid which precipitated was collected by filtration, washed with water, and recrystallized from 2-propanol and then from cyclohexane to yield 16.4 g (34%) of crystals, m.p. 134°–136° C.

Analysis: Calculated for $C_{14}H_{10}ClNO$: C,69.00; H,4.14; N,5.75. Found: C,69.13; H,4.14; N,5.87.

INTERMEDIATE 30

3-(4-Chlorophenyl)-7-(bromomethyl)-2,1-benzisoxazole

A mixture of 15.7 g (0.065 mole) of 3-(4-chlorophenyl)-7-methyl-2,1-benzisoxazole, 11.6 g (0.065 mole) of N-bromosuccinimide, 0.5 g of dibenzoylperoxide and 400 ml of carbon tetrachloride was heated at reflux while being illuminated by a flood lamp for 3 hr. The mixture was filtered and the filtrate was concentrated to give a solid as residue. The solid was recrystallized three times from acetonitrile to yield 12.0 g (58%) of crystals, m.p. 153°–155° C.

Analysis: Calculated for $C_{14}H_9BrClNO$: C,52.13; H,2.81; N,4.34. Found: C,52.25; H,2.82; N,4.42.

INTERMEDIATE 31

3-(4-Chlorophenyl)-2,1-benzisoxazol-7-acetonitrile

A solution of 11.5 g (0.036 mole) of crude 3-(4-chlorophenyl)-7-(bromomethyl)-2,1-benzisoxazole, 9.8 g (0.15 mole) of potassium cyanide, 150 ml of dioxane and 75 ml of water was heated at reflux under a nitrogen atmosphere for 2.5 hr. The solution was cooled and poured into 400 ml of methylene chloride. The layers were separated and the organic layer was washed with four 200 ml portions of water, dried over sodium sulfate, and concentrated to give a solid as residue. The solid was recrystallized (charcoal) twice from ethyl acetate to yield 5.8 g (61%) of crystals, m.p. 165°–169° C.

Analysis: Calculated for $C_{15}H_9ClN_2O$: C,67.05; H,3.38; N,10.43. Found: C,67.20; H,3.36; N,10.33.

INTERMEDIATE 32

3-(4-Bromophenyl)-7-methyl-2,1-benzisoxazole

A solution of 130 ml of 30% hydrogen peroxide in 350 ml of glacial acetic acid was heated on a steam bath for 1 hr. To the cooled solution was added a solution of 31.0 g (0.11 mole) of (2-amino-3-methylphenyl)(4-bromophenyl)methanone in 400 ml of glacial acetic acid. The reaction mixture was heated to 95° C. to dissolve all solids, then heated at 65°–70° C. for 4 hr and let stand at ambient temperature overnight.

The reaction mixture was poured into 2.5 liters of ice water, let stand for 4 hr and filtered. The filter cake was washed with 400 ml of water and air dried to give 14.7 g of solid. A 1.0 g sample of solid was twice recrystallized from 2-propanol to give 0.4 g (21%) of fluffy, yellow crystals, m.p. 126°–128° C.

Analysis: Calculated for $C_{14}H_{10}BrNO$: C,58.36; H,3.50; N,4.86. Found: C,58.28; H,3.45; N,4.88.

INTERMEDIATE 33

7-(Bromomethyl)-3-(4-bromophenyl)-2,1-benzisoxazole

A mixture of 6.4 g (0.0222 mole) of (4-bromophenyl)-7-methyl-2,1-benzisoxazole, 4.0 g (0.0225 mole) of N-bromosuccinimide and 0.1 g of dibenzoyl peroxide in 250 ml of carbon tetrachloride was heated at reflux for 3 hr under flood light illumination and an argon atmosphere, and filtered while still hot. The filtrate was washed twice with 200 ml portions of 10% sodium bicarbonate solution and twice with 200 ml portions of water and dried over sodium sulfate. The sodium sulfate was removed by filtration and the filtrate was concentrated under reduced pressure to a solid residue. The solid was recrystallized from 2-propanol to give 5.9 g (73%) of fluffy yellow crystals, m.p. 159°–161° C.

Analysis: Calculated for $C_{14}H_9Br_2NO$: C,45.81; H,2.47; N,3.82. Found: C,45.67; H,2.47; N,3.81.

INTERMEDIATE 34

3-(4-Bromophenyl)-2,1-benzisoxazole-7-acetonitrile

A solution of 2.9 g (0.0186 mole) of tetraethylammonium cyanide in 30 ml of methylene chloride was heated to reflux under an argon atmosphere. To this stirred solution was added, dropwise, a solution of 5.7 g (0.0155 mole) of 7-(bromomethyl)-3-(4-bromophenyl)-2,1-benzisoxazole in 100 ml of methylene chloride. The reaction mixture was heated at reflux for 2.5 hr. The solvent was evaporated under reduced pressure and the dark semi-solid pot residue was purified by chromatography (3.5×60 cm glass column; 175 g of silica gel; benzene). Fractions containing the title compound were combined and the solvent was evaporated under reduced pressure to give 3.8 g of solid. The solid was recrystallized from benzene to give 3.7 g (75%) of tiny orange needles, m.p. 177°–180° C.

Analysis: Calculated for $C_{15}H_9BrN_2O$: C,57.53; H,2.90; N,8.95. Found: C,57.41; H,2.88; N,8.91.

INTERMEDIATE 35

3-(2,4-Dichlorophenyl)-7-methyl-2,1-benzisoxazole

A solution of 300 ml of glacial acetic acid and 150 ml of 30% hydrogen peroxide was heated on a steam bath for 1 hr, cooled, and treated with 30.8 g (0.11 mole) of 2-amino-3-methylphenyl)(2,4-dichlorophenyl)methanone. The mixture was heated at 60° C. and 200 ml of acetic acid was added to dissolve all solids. The solution was heated at 60° C. for 5 hr and let stand at ambient temperature overnight. The mixture was poured into 2.5 liters of water and the solid was collected by filtration, washed with water and dried. The solid was recrystallized from 2-propanol to yield 12.0 g (39%) of tan solid, m.p. 94°–95° C.

Analysis: Calculated for $C_{14}H_9Cl_2NO$: C,60.46; H,3.26; N,5.04. Found: C,60.37; H,3.24; N,5.18.

INTERMEDIATE 36

7-(Bromomethyl)-3-(2,4-dichlorophenyl)-2,1-benzisoxazole

A mixture of 10.9 g (0.039 mole) of 3-(2,4-dichlorophenyl)-7-methyl-2,1-benzisoxazole, 7.1 g (0.040 mole) of N-bromosuccinimide, 0.1 g of dibenzoylperoxide and 200 ml of carbon tetrachloride was heated at reflux under illumination of a flood lamp for 2 hr. The mixture was filtered and the filtrate was washed once with a saturated sodium bicarbonate solution, dried over sodium sulfate and concentrated to give a solid as residue. The solid was recrystallized from 2-propanol to yield 10.0 g (71%) of tan solid, m.p. 108°–110° C.

Analysis: Calculated for $C_{14}H_8BrCl_2NO$: C,47.10; H,2.26; N,3.92. Found: C,47.21; H,2.24; N,3.90.

INTERMEDIATE 37

3-(2,4-Dichlorophenyl)-2,1-benzisoxazole-7-acetonitrile

To a slurry of 1.8 g (0.028 mole) of potassium cyanide in 80 ml of dimethylsulfoxide at 60° C. was added 9.7 g (0.027 mole) of 7-(bromomethyl)-3-(2,4-dichlorophenyl)-2,1-benzisoxazole. The mixture was heated at 50°–60° C. for 3 hr, poured into 1 liter of water and let stand overnight. The resulting solid was collected by filtration, washed with water and dried to give 7.6 g of crude tan solid. The solid was chromatographed on 160 g of silica gel to give 2.7 g of solid. The solid was recrystallized from carbon tetrachloride (charcoal) and then from acetonitrile to yield 0.7 g (8%) of crystals, m.p. 147°–148° C.

Analysis: Calculated for $C_{15}H_8Cl_2N_2O$: C,59.43; H,2.66; N,9.24. Found: C,59.21; H,2.62; N,9.41.

INTERMEDIATE 38

5-Chloro-7-methyl-3-phenyl-2,1-benzisoxazole

A solution of 175 ml of 30% hydrogen peroxide and 600 ml of glacial acetic acid was heated on a steam bath for 1 hr and cooled. The solution was treated with 36.8 g (0.15 mole) of (2-amino-5-chloro-3-methylphenyl)-phenylmethanone and the mixture was heated at 55°–70° C. for 7 hr and let stand overnight at ambient temperature. The mixture was diluted with 2 liters of water and the solid was collected by filtration, washed with water and dried. The solid was recrystallized from 2-propanol to yield 18.2 g (50%) of pale-yellow needles, m.p. 108°–109° C.

Analysis: Calculated for $C_{14}H_{10}ClNO$: C,69.00; H,4.14; N,5.75. Found: C,68.98; H,4.13; N,5.83.

INTERMEDIATE 39

7-(Bromomethyl)-5-chloro-3-phenyl-2,1-benzisoxazole

A mixture of 16.2 g (0.067 mole) of 5-chloro-7-methyl-3-phenyl-2,1-benzisoxazole, 11.9 g (0.067 mole) of N-bromosuccinimide, 275 ml of carbon tetrachloride and 0.1 g of dibenzoylperoxide was heated at reflux under illumination of a flood lamp for 2 hr. The mixture was filtered and the filtrate was washed once with a saturated sodium bicarbonate solution, dried over sodium sulfate and concentrated to give a yellow solid as residue. An NMR analysis of the residue showed it was a mixture containing 8% of starting methyl compound, 83% of monobromo compound and 9% of dibromo compound. An analytical sample, m.p. 142°–144° C., was obtained by recrystallizing twice from ethyl acetate.

Analysis: Calculated for $C_{14}H_9BrClNO$: C,52.13; H,2.81; N,4.34. Found: C,52.18; H,2.80; N,4.38.

INTERMEDIATE 40

5-Chloro-3-phenyl-2,1-benzisoxazole-7-acetonitrile

A mixture of 18.7 g (0.058 mole) of crude 7-(bromomethyl)-5-chloro-3-phenyl-2,1-benzisoxazole, 13 g (0.20 mole) of potassium cyanide, 200 ml of dioxane and 100 ml of water was heated at reflux under a nitrogen atmosphere for 2.5 hr. The volume of the reaction mixture was reduced to 150 ml by distillation and then was diluted with 350 ml of methylene chloride. The layers were separated and the organic layer was washed twice with water, dried (sodium sulfate) and concentrated to give 14.1 g dark green gum as residue. The residue was chromatographed on 300 g of silica gel to give 4.7 g (36%) of orange solid. An analytical sample, m.p. 158°–159° C. was prepared by successive recrystallizations of the orange solid from benzene-cyclohexane, acetonitrile (charcoal) and finally from benzene.

Analysis: Calculated for $C_{15}H_9ClN_2O$: C,67.05; H,3.38; N,10.43. Found: C,67.12; H,3.36; N,10.61.

INTERMEDIATE 41

5-Chloro-3-(4-chlorophenyl)-7-methyl-2,1-benzisoxazole

A solution of 300 ml of glacial acetic acid and 150 ml of 30% hydrogen peroxide was heated on a steam bath for 1 hr, cooled, and treated with 28.0 g (0.1 mole) of (2-amino-5-chloro-3-methylphenyl)(4-chlorophenyl)methanone. The mixture was heated to 95° C. and 450 ml of acetic acid was added to dissolve all solids. The stirred mixture was heated at 60°–70° C. for 5 hr, poured into 2.5 liters of water and let stand at ambient temperature overnight. The solid was collected by filtration, washed with water and recrystallized from 2-propanol to yield 12.3 g (44%) of fluffy, off-white solid, m.p. 151°–152° C.

Analysis: Calculated for $C_{14}H_9Cl_2NO$: C,60.46; H,3.26; N,5.04. Found: C,60.57; H,3.23; N,5.17.

INTERMEDIATE 42

7-(Bromomethyl)-5-chloro-3-(4-chlorophenyl)-2,1-benzisoxazole

A mixture of 12.2 g (0.044 mole) of 5-chloro-3-(4-chlorophenyl)-7-methyl-2,1-benzisoxazole, 8.0 g (0.045 mole) of N-bromosuccinimide, 0.1 g of dibenzoylperoxide and 500 ml of carbon tetrachloride was heated at reflux under white light illumination for 2 hr. The hot mixture was filtered and the filtrate was washed once with sodium bicarbonate solution, dried (sodium sulfate) and concentrated to give a solid as residue. The solid was recrystallized from acetonitrile to give 12.8 g (81%) of crude product. A portion of the solid was chromatographed on silica gel. The purified product was recrystallized from acetonitrile to yield an analytical sample of pale yellow solid, m.p. 145°–147° C.

Analysis: Calculated for $C_{14}H_8BrCl_2NO$: C,47.10; H,2.26; N,3.92. Found: C,47.31; H,2.28; N,4.05.

INTERMEDIATE 43

5-Chloro-3-(4-chlorophenyl)-2,1-benzisoxazole-7-acetonitrile

This compound was prepared by the procedure used to synthesize the compound of Intermediate 28. The reaction of 6.2 g (0.0397 mole) of tetraethylammonium cyanide and 10.0 g (0.028 mole) of 7-(bromomethyl)-3-(4-chlorophenyl)-5-chloro-2,1-benzisoxazole in 130 ml of methylene chloride gave 7.8 g of a dark semi-solid residue. The solid was purified by chromatography (3.5×60 cm glass column; 180 g of silica gel; benzene). Fractions containing the title compound were combined and the solvent removed under reduced pressure to give 1.5 g of solid. The solid was dissolved in 40 ml of methylene chloride, treated with charcoal, and filtered. The filtrate was evaporated to a solid residue. The solid was recrystallized from benzene-petroleum ether (30°–60° C.) to give 1.3 g (16%) of a yellow solid, m.p. 187°–190° C.

Analysis: Calculated for $C_{15}H_8Cl_2N_2O$: C,59.43; H,2.66 N,9.24. Found: C,59.20; H,2.68; N,8.96.

INTERMEDIATE 44

3-(4-Bromophenyl)-5-chloro-7-methyl-2,1-benzisoxazole

A solution of 130 ml of 30% hydrogen peroxide in 350 ml of glacial acetic acid was heated on a steam bath for 1 hr and then cooled. To the cooled solution was added 31.0 g (0.0955 mole) of (2-amino-5-chloro-3-methylphenyl)(4-bromophenyl)methanone followed by 450 ml of glacial acetic acid. The reaction mixture was heated to 95° C. to dissolve all solids, heated at 65°–70° C. for 8 hr and then cooled. The reaction mixture was poured into 2.5 liters of ice water and let stand at ambient temperature for 3 hr and filtered. The filter cake was washed with 500 ml of 10% sodium bicarbonate solution and 500 ml of water and dried to give 22.5 g of solid. The solid was recrystallized from 2-propanol to give 20.5 g (67%) of fluffy yellow needles, m.p. 163°–165° C.

Analysis: Calculated for $C_{14}H_9BrClNO$: C,52.13; H,2.81; N,4.34. Found: C,52.05; H,2.82; N,4.36.

INTERMEDIATE 45

7-(Bromomethyl)-3-(4-bromophenyl)-5-chloro-2,1-benzisoxazole

A mixture of 2.1 g (0.0065 mole) of 3-(4-bromophenyl)-5-chloro-7-methyl-2,1-benzisoxazole, 1.2 g (0.0067 mole) of N-bromosuccinimide and a few crystals of dibenzoyl peroxide in 100 ml of carbon tetrachloride was heated at reflux for 2.5 hr under flood light illumination and an argon atmosphere and then filtered while still hot. The filtrate was concentrated under reduced pressure to a solid residue. The solid was recrystallized twice from 2-propanol to give 2.2 g (85%) of light-yellow needles, m.p. 147°–150° C.

INTERMEDIATE 46

3-(4-Bromophenyl)-5-chloro-2,1-benzisoxazole-7-acetonitrile

A solution of 2.9 g (0.0186 mole) of tetraethylammonium cyanide in 30 ml of methylene chloride was heated at reflux under an argon atmosphere. To this solution was added a solution of 6.5 g (0.0162 mole) of 7-(bromomethyl)-3-(4-bromophenyl)-5-chloro-2,1-benzisoxazole in 100 ml of methylene chloride. The reaction mixture was heated at reflux for 3 hr. The solvent was evaporated under reduced pressure and the dark, solid residue was triturated with 1.5 liter of diethyl ether and filtered. The filtrate was evaporated under reduced pressure to give 2.5 g of a solid. The solid was recrystallized twice from benzene-petroleum ether (30°-60° C.) to give 0.6 g (11%) of light-yellow solid, m.p. 199°-201° C.[1]

[1] An additional 1.5 g of title compound was recovered from the mother liquor by chromatography. Total yield 2.1 g (37%).

Analysis: Calculated for $C_{15}H_8BrClN_2O$: C,51.83; H,2.32; N,8.06. Found: C,51.63; H,2.37; N,7.79.

INTERMEDIATE 47

7-Methyl-3-[4-(trifluoromethyl)phenyl]-2,1-benzisoxazole

A solution of 150 ml of 30% hydrogen peroxide and 300 ml of glacial acetic acid was heated on a steam bath for 1 hr and then cooled. The solution was treated with 26.3 g (0.094 mole) of (2-amino-3-methylphenyl) [4-(trifluoromethyl)phenyl]methanone and the mixture was heated at 70° C. for 7 hr and let stand at ambient temperature overnight. The mixture was poured into 2 liters of ice water and the solid was collected by filtration, washed with water and recrystallized from 2-propanol to yield 3.4 g (13%) of tan powder, m.p. 118°-119° C.

Analysis: Calculated for $C_{15}H_{10}F_3NO$: C,64.98; H,3.64; N,5.05. Found: C,64.89; H,3.62; N,5.07.

INTERMEDIATE 48

7-(Bromomethyl)-3-(4-trifluoromethyl)-2,1-benzisoxazole

Following the procedure of Intermediate 45, the title compound is prepared by reacting 7-methyl-3-[4-(trifluoromethyl)phenyl]-2,1-benzisoxazole with N-bromosuccinimide.

INTERMEDIATE 49

3-(4-Trifluoromethyl)-2,1-benzisoxazole-7-acetonitrile

Following the procedure of Intermediate 46, the title compound is prepared by reacting 7-(bromomethyl)-3-(4-trifluoromethyl)-2,1-benzisoxazole with tetraethylammonium cyanide.

INTERMEDIATE 50

2-Amino-3-benzoyl-α-(methylthio)benzeneacetonitrile

To a slurry of 29.6 g (0.15 mole) of 2-aminobenzophenone and 13.1 g (0.15 mole) of (methylthio)acetonitrile in 400 ml of methylene dichloride at a temperature of −68° C. was added dropwise 16.8 g (0.155 mole) of t-butyloxychloride at a rate to ensure that the reaction temperature did not exceed −64° C. The resulting solution was stirred at −69° C. for one hour, treated with 15.7 g (0.155 mole) of triethylamine and allowed to warm to ambient temperature. The solution obtained was washed twice with water, dried over sodium sulphate, and concentrated to give 45.2 g of a dark oil as the residue. This residue was chromatographed on 1 kg of silica gel to yield 22.5 g (53%) of the title compound as tan crystals, m.p. 107°-108° C.

Analysis: Calculated for $C_{16}H_{14}N_2OS$: C,68.06; H,5.00; N,9.92. Found: C,68.39; H,5.00; N,10.06.

INTERMEDIATE 51

2-Amino-3-(4-chlorobenzoyl)-α-(methylthio)benzeneacetonitrile

To a solution of 46.3 g (0.2 mole) of 4'-chloro-2-aminobenzophenone and 17.4 g (0.2 mole) of methylthioacetonitrile in 1 liter of methylene dichloride at a temperature of −70° C. was added dropwise 22.2 g (0.21 mole) of tert. butyloxychloride at a rate to ensure that the reaction temperature did not exceed −65° C. The resulting solution was allowed to warm to ambient temperature, washed twice with water, dried over sodium sulphate, and concentrated to give a gum residue. The gum crystallized when it was triturated with diethyl ether. The solid was collected by filtration and recrystallized from 2-propanol to yield 43.0 g (68%) of the title compound as a tan solid, m.p. 122° C.

Analysis: Calculated for $C_{16}H_{13}ClN_2OS$: C,60.66; H,4.14; N,8.84. Found: C,60.71; H,4.17; N,8.88.

INTERMEDIATE 52

Utilizing the procedure of Intermediate 50 and substituting the following for 2-aminobenzophenone:
2-amino-3',4'-dimethoxybenzophenone,
2-amino-4'-fluorobenzophenone,
2-amino-4'-methoxybenzophenone,
2-amino-4'-iodobenzophenone,
2-amino-4'-bromobenzophenone,
2-amino-4'-bromo-5-chlorobenzophenone,
2-amino-4'-bromo-5-fluorobenzophenone,
2-amino-4'-fluoro-5-methylbenzophenone,
2-amino-2',4'-dichloro-5-methylbenzophenone,
2-amino-4'-bromo-5-methylbenzophenone,
2-amino-2',5-dichloro-4'-bromobenzophenone,
2-amino-2'-chloro-4'-bromobenzophenone,
2-amino-3',4',5'-trimethoxybenzophenone,
2-amino-5-chloro-4'-methylbenzophenone,
2-amino-5-chloro-4'-trifluoromethylbenzophenone, and
2-amino-5-trifluoromethylbenzophenone,
there are obtained:
2-amino-3-(3,4-dimethoxybenzoyl)-α-(methylthio)benzeneacetonitrile,
2-amino-3-(4-fluorobenzoyl)-α-(methylthio)benzeneacetonitrile,
2-amino-3-(4-methoxybenzoyl)-α-(methylthio)benzeneacetonitrile,
2-amino-3-(4-iodobenzoyl)-α-(methylthio)benzeneacetonitrile,
2-amino-3-(4-bromobenzoyl)-α-(methylthio)benzeneacetonitrile,
2-amino-3-(4-bromobenzoyl)-5-chloro-α-(methylthio)benzeneacetonitrile,
2-amino-3-(4-bromobenzoyl)-5-fluoro-α-(methylthio)benzeneacetonitrile,
2-amino-3-(4-fluorobenzoyl)-5-methyl-α-(methylthio)benzeneacetonitrile,
2-amino-3-(2,4-dichlorobenzoyl)-5-methyl-α-(methylthio)benzeneacetonitrile,
2-amino-3-(4-bromobenzoyl)-5-methyl-α-(methylthio)benzeneacetonitrile, 2-amino-3-(2-chloro-4-bromobenzoyl)-5-chloro-α-(methylthio)benzeneacetonitrile,
2-amino-3-(2-chloro-4-bromobenzoyl)-α-(methylthio)benzeneacetonitrile,
2-amino-3-(3,4,5-trimethoxybenzoyl)-α-(methylthio)benzeneacetonitrile,
2-amino-5-chloro-3-(4-methylbenzoyl)-α-(methylthio)benzeneacetonitrile,
2-amino-5-chloro-3-[4-(trifluoromethyl)benzoyl]-α-(methylthio)benzeneacetonitrile, and
2-amino-5-trifluoromethyl-3-benzoyl-α-(methylthio)benzeneacetonitrile.

INTERMEDIATE 53

Utilizing the procedure of Intermediate 50 and substituting the following for methylthioacetonitrile:
(ethylthio)acetonitrile,
(butylthio)acetonitrile,
(phenylthio)acetonitrile,
(phenylmethylthio)acetonitrile,
(phenylethylthio)acetonitrile, and
(4-methylphenylthio)acetonitrile,
there are obtained:
2-amino-3-benzoyl-α-(ethylthiobenzeneacetonitrile,
2-amino-3-benzoyl-α-(butylthio)benzeneacetonitrile,
2-amino-3-benzoyl-α-(phenylthio)benzeneacetonitrile,
2-amino-3-benzoyl-α-[(phenylmethyl)thio]benzeneacetonitrile,
2-amino-3-benzoyl)-α-[(phenylethyl)thio]benzeneacetonitrile, and
2-amino-3-benzoyl-α-[(4-methylphenyl)thio]benzeneacetonitrile.

INTERMEDIATE 54

2-Amino-3-benzoyl-5-methoxy-α-(methylthio)benzeneacetonitrile

To a solution of 4.0 ml (0.088 mole) of chlorine in 200 ml of methylene chloride cooled to −70° C. is added dropwise a solution of 7.65 g (0.088 mole) of methylthioacetonitrile in 1 liter of methylene chloride while maintaining the temperature below −65° C. After several minutes a solution containing 0.2 mole of 2-amino-5-methoxybenzophenone in 100 ml of methylene chloride is added dropwise over a 30 min period. The mixture is stirred at −70° C. for about 1.5 hr and 18 g (0.18 mole) of triethylamine is added. The mixture is stirred for about an hour at −70° C. and then allowed to warm to ambient temperature. The mixture is washed with water, dried over sodium sulfate and concentrated under reduced pressure. The residue is recrystallized from a suitable solvent, e.g., 2-propanol, to give the title product.

INTERMEDIATE 55

2-Amino-3-benzoylbenzeneacetonitrile

To a solution of 19.4 g (0.069 mole) of 2-amino-3-benzoyl-α-(methylthio)benzeneacetonitrile in 200 ml of tetrahydrofuran was added 160 g of commercial Raney nickel which had been washed three times with water and three times with tetrahydrofuran. The mixture was stirred at ambient temperature for 10 minutes and then filtered. The filtrate obtained was concentrated to give a solid residue. This residue was recrystallized from 2-propanol to yield 11.7 g (72%) of the titled compound as bronze needles, m.p. 137.5°–139° C.

Analysis: Calculated for $C_{12}H_{12}N_2O$: C,76.25; H,5.12; N,11.86. Found: C,76.20; H,5.09; N,11.82.

INTERMEDIATE 56

2-Amino-3-(4-chlorobenzoyl)benzeneacetonitrile

A 280 g sample of a commercial Raney nickel preparation was washed twice with water, titrated to a pH of 7 with acetic acid, washed twice with water and three times with tetrahydrofuran. The Raney nickel preparation was then slurried in 300 ml of tetrahydrofuran and added to a stirred solution of 34.4 g (0.11 mole) of 2-amino-3-(4-chlorobenzoyl)-α-(methylthio)benzeneacetonitrile in 250 ml of tetrahydrofuran. The resulting mixture was stirred at ambient temperature for 10 minutes, filtered through Celite, and the filtrate concentrated to give a solid as a residue. This solid residue was recrystallized from acetonitrile to yield 16.4 g (56%) of the titled compound as brown crystals, m.p. 181°–2° C.

Analysis: Calculated for $C_{15}H_{11}ClN_2O$: C,66.55; H,4.10; N,10.35. Found: C,66.59; H,4.10; N,10.46.

INTERMEDIATE 57

Utilizing the procedure of Intermediate 55 and substituting the following for 2-amino-3-benzoyl-α-(methylthio)benzeneacetonitrile:
2-amino-3-benzoyl-5-methoxy-α-(methylthio)benzeneacetonitrile,
2-amino-3-(3,4-dimethoxybenzoyl)-α-(methylthio)benzeneacetonitrile,
2-amino-3-(4-fluorobenzoyl)-α-(methylthio)benzeneacetonitrile,
2-amino-3-(4-methoxybenzoyl)-α-(methylthio)benzeneacetonitrile,
2-amino-3-(4-iodobenzoyl)-α-(methylthio)benzeneacetonitrile,
2-amino-3-(4-bromobenzoyl)-α-(methylthio)benzeneacetonitrile,
2-amino-3-(4-bromobenzoyl)-5-chloro-α-(methylthio)benzeneacetonitrile,
2-amino-3-(4-bromobenzoyl)-5-fluoro-α-(methylthio)benzeneacetonitrile,
2-amino-3-(4-fluorobenzoyl)-5-methyl-α-(methylthio)benzeneacetonitrile,
2-amino-3-(2,4-dichlorobenzoyl)-5-methyl-α-(methylthio)benzeneacetonitrile,
2-amino-3-(4-bromobenzoyl)-5-methyl-α-(methylthio)benzeneacetonitrile,
2-amino-3-(2-chloro-4-bromobenzoyl)-5-chloro-α-(methylthio)benzeneacetonitrile,
2-amino-3-(2-chloro-4-bromobenzoyl)-α-(methylthio)benzeneacetonitrile,
2-amino-3-(3,4,5-trimethoxybenzoyl)-α-(methylthio)benzeneacetonitrile,
2-amino-5-chloro-3-(4-methylbenzoyl)-α-(methylthio)benzeneacetonitrile,
2-amino-5-chloro-3-[4-(trifluoromethyl)benzoyl]-α-(methylthio)benzeneacetonitrile, and
2-amino-5-trifluoromethyl-3-benzoyl-α-(methylthio)benzeneacetonitrile,
there are obtained:
2-amino-3-benzoyl-5-methoxybenzeneacetonitrile,
2-amino-3-(3,4-dimethoxybenzoyl)benzeneacetonitrile,
2-amino-3-(4-fluorobenzoyl)benzeneacetonitrile,
2-amino-3-(4-methoxybenzoyl)benzeneacetonitrile,
2-amino-3-(4-iodobenzoyl)benzeneacetonitrile,
2-amino-3-(4-bromobenzoyl)benzeneacetonitrile,
2-amino-3-(4-bromobenzoyl)-5-chlorobenzeneacetonitrile, 2-amino-3-(4-bromobenzoyl)-5-fluorobenzeneacetonitrile,
2-amino-3-(4-fluorobenzoyl)-5-methylbenzeneacetonitrile,
2-amino-3-(2,4-dichlorobenzoyl)-5-methylbenzeneacetonitrile,
2-amino-3-(4-bromobenzoyl)-5-methylbenzeneacetonitrile,
2-amino-3-(2-chloro-4-bromobenzoyl)-5-chlorobenzeneacetonitrile,
2-amino-3-(2-chloro-4-bromobenzoyl)benzeneacetonitrile,
2-amino-3-(3,4,5-trimethoxybenzoyl)benzeneacetonitrile,
2-amino-5-chloro-3-(4-methylbenzoyl)benzeneacetonitrile,
2-amino-5-chloro-3-[4-(trifluoromethyl)benzoyl]benzeneacetonitrile, and
2-amino-5-trifluoromethyl-3-(4-chlorobenzoyl)benzeneacetonitrile.

INTERMEDIATE 58

2-Amino-3-benzoylbenzeneacetonitrile

Utilizing the procedure of Intermediate 55 and substituting any one of the following for 2-amino-3-benzoyl-α-(methylthio)benzeneacetonitrile:
2-amino-3-benzoyl-α-(ethylthio)benzeneacetonitrile,
2-amino-3-benzoyl-α-(butylthio)benzeneacetonitrile,
2-amino-3-benzoyl-α-(phenylthio)benzeneacetonitrile,
2-amino-3-benzoyl-α-[(phenylmethyl)thio]benzeneacetonitrile,
2-amino-3-benzoyl-α-[(phenylethyl)thio]benzeneacetonitrile, and
2-amino-3-benzoyl-α-[(4-methylphenyl)thio]benzeneacetonitrile.
the title compound is produced.

INTERMEDIATE 59

3-Phenyl-2,1-benzisoxazol-7-acetonitrile (See Chart II, Method A)

A mixture of 12.3 g (0.052 mole) of 2-amino-3-benzoylbenzeneacetonitrile, 23.9 g (0.156 mole) of sodium perborate tetrahydrate and 145 ml of acetic acid was heated at 70° C. overnight. The mixture was poured into a mixture of 1500 ml of ice and water. A solid gradually precipitated. The solid was collected and recrystallized from 250 ml of isopropyl alcohol to give 7.8 g (64%) of tan solid, m.p. 141°-144° C. The NMR analysis indicated the product had the same characteristics as in Intermediate 22.

INTERMEDIATE 60

3-(4-Chlorophenyl)-2,1-benzisoxazole-7-acetonitrile

Following the procedure of Intermediate 59, 2-amino-3-(4-chlorobenzoyl)benzeneacetonitrile is reacted with sodium perborate tetrahydrate in acetic acid at 70° C. and thereafter mixed with ice-water to obtain the title compound.

INTERMEDIATE 61

Following the procedure of Intermediate 59, the following are reacted with sodium perborate tetrahydrate in acetic acid at 70° C. and thereafter mixed with ice-water:
2-amino-3-benzoyl-5-methoxybenzeneacetonitrile,
2-amino-3-(3,4-dimethoxybenzoyl)benzeneacetonitrile,
2-amino-3-(4-fluorobenzoyl)benzeneacetonitrile,
2-amino-3-(4-methoxybenzoyl)benzeneacetonitrile,
2-amino-3-(4-iodobenzoyl)benzeneacetonitrile,
2-amino-3-(4-bromobenzoyl)benzeneacetonitrile,
2-amino-3-(4-bromobenzoyl)-5-chlorobenzeneacetonitrile,
2-amino-3-(4-bromobenzoyl)-5-fluorobenzeneacetonitrile,
2-amino-3-(4-fluorobenzoyl)-5-methylbenzeneacetonitrile,
2-amino-3-(2,4-dichlorobenzoyl)-5-methylbenzeneacetonitrile,
2-amino-3-(4-bromobenzoyl)-5-methylbenzeneacetonitrile,
2-amino-3-(2-chloro-4-bromobenzoyl)-5-chlorobenzeneacetonitrile,
2-amino-3-(2-chloro-4-bromobenzoyl)benzeneacetonitrile,
2-amino-3-(3,4,5-trimethoxybenzoyl)benzeneacetonitrile,
2-amino-5-chloro-3-(4-methylbenzoyl)benzeneacetonitrile,
2-amino-5-chloro-3-[4-(trifluoromethyl)benzoyl]benzeneacetonitrile, and
2-amino-5-trifluoromethyl-3-(4-chlorobenzoyl)benzeneacetonitrile,
to give:
(a) 3-phenyl-5-methoxy-2,1-benzisoxazol-7-acetonitrile,
(b) 3-(3,4-dimethoxyphenyl)-2,1-benzisoxazole-7-acetonitrile,
(c) 3-(4-fluorophenyl)-2,1-benzisoxazole-7-acetonitrile,
(d) 3-(4-methoxyphenyl)-2,1-benzisoxazole-7-acetonitrile,
(e) 3-(4-iodophenyl)-2,1-benzisoxazole-7-acetonitrile,
(f) 3-(4-bromophenyl)-2,1-benzisoxazole-7-acetonitrile,
(g) 3-(4-bromophenyl)-5-chloro-2,1-benzisoxazole-7-acetonitrile,
(h) 3-(4-bromophenyl)-5-fluoro-2,1-benzisoxazole-7-acetonitrile,
(i) 3-(4-fluorophenyl)-5-methyl-2,1-benzisoxazole-7-acetonitrile,
(j) 3-(2,4-dichlorophenyl)-5-methyl-2,1-benzisoxazole-7-acetonitrile,
(k) 3-(4-bromophenyl)-5-methyl-2,1-benzisoxazole-7-acetonitrile,
(l) 3-(4-bromo-2-chlorophenyl)-5-chloro-2,1-benzisoxazole-7-acetonitrile,
(m) 3-(4-bromo-2-chlorophenyl)-2,1-benzisoxazole-7-acetonitrile,
(n) 3-(3,4,5-trimethoxyphenyl)-2,1-benzisoxazole-7-acetonitrile,
(o) 5-chloro-3-(4-methylphenyl)-2,1-benzisoxazole-7-acetonitrile,
(p) 5-chloro-3-[4-(trifluoromethyl)phenyl]-2,1-benzisoxazole-7-acetonitrile, and
(q) 3-(4-chlorophenyl)-5-trifluoromethyl-2,1-benzisoxazole-7-acetonitrile.

INTERMEDIATE 62

3-(4-Chlorobenzoyl)-4-nitrobenzene acetic acid

To a solution of 0.0175 mole of diethylsodiomalonate in 250 ml of diethyl malonate under nitrogen atmosphere at 80° C. was added 20.7 g (0.07 mole) of 4',5-dichloro-2-nitrobenzophenone. The mixture was heated at 90° C. for 2 hr, then poured into water and neutralized with glacial acetic acid. The mixture was extracted with diethyl ether and then washed and dried over sodium sulfate; extracts were concentrated and excess diethyl malonate removed by distillation. The residue was chromatographed eluting with 50–75% isopropyl ether in hexane and the appropriate fraction collected. This material was hydrolyzed by heating at reflux in a mixture of 150 ml of dioxane and 80 ml of 6N hydrochloric acid for 6 hr. The reaction mixture was diluted with water and extracted with diethyl ether. The ether extracts were washed with dilute sodium hydroxide and the basic washings were combined, acidified and extracted with diethyl ether-isopropyl ether to give after recrystallization from 80% aqueous methanol, 6.2 g of title compound as tan crystals, m.p. 182.0°–183.0° C.

Analysis: Calculated for $C_{15}H_{10}ClNO_5$: C,56.35; H,3.15; N,4.38. Found: C,56.19; H,3.13; N,4.36.

INTERMEDIATE 63

3-(4-Chlorobenzoyl)-4-nitrobenzene acetamide

A mixture of 3-(4-chlorobenzoyl)-4-nitrobenzene acetic acid 5.7 g (0.018 mole) and 25 ml of thionyl chloride was heated at reflux for 1.5 hr. Excess thionyl chloride was removed by distillation and azeotroped with benzene. The residue was dissolved in methylene chloride and poured rapidly into stirring concentrated ammonium hydroxide (200 ml). The mixture was stirred for 15 minutes, then the solid was collected and the organic phase was separated; the organic layer and solid layer were combined and concentrated. The residue was recrystallized with charcoal treatment from 3:1 isopropanol:ethanol to give 4.8 g (84%) of the title compound as white needles, m.p. 211.5°–212.5° C.

Analysis: Calculated for $C_{15}H_{11}ClN_2O_4$: C,56.53; H,3.48; N,8.79. Found: C,56.45; H,3.46; N,8.80.

EXAMPLE 1

3-(2,1-Benzisoxazol-3-yl)benzeneacetic acid

A mixture of 5.9 g (0.025 mole) of 3-(2,1-benzisoxazol-3-yl)benzeneacetonitrile, 150 ml of ethanol and 20 ml of 20% sodium hydroxide was heated at reflux under a nitrogen atmosphere overnight. The red solution was concentrated and the residue was dissolved in 600 ml of water. The solution was filtered through Celite and the filtrate was treated with charcoal and again filtered through Celite. The filtrate was made acidic with concentrated hydrochloric acid and a gum precipitated. The gum gradually crystallized. The solid was collected by filtration, washed with water and recrystallized from 2-propanol to yield 5.1 g (80%) of tan powder, m.p. 143°–145° C.

Analysis: Calculated for $C_{15}H_{11}NO_3$: C,71.14; H,4.38; N,5.53. Found: C,71.26; H,4.40; N,5.56.

EXAMPLE 2

4-(2,1-Benzisoxazol-3-yl)benzeneacetic acid

A solution of 3.6 g (0.015 mole) of 4-(2,1-benzisoxazol-3-yl)benzeneacetonitrile in 75 ml of ethanol and 10 ml of 20% sodium hydroxide was heated at reflux under a nitrogen atmosphere overnight. The dark solution was cooled and poured into 600 ml of water. The solution was filtered and the filtrate was treated with charcoal. The mixture was filtered through Celite and the filtrate pH was adjusted to 7. The mixture was again filtered and the filtrate was made acidic with concentrated hydrochloric acid. The solid which precipitated was collected by filtration, washed with water, dried, and recrystallized from 2-propanol to yield 2.1 g (54%) of tan powder, m.p. 179°–181° C. with decomposition.

Analysis: Calculated for $C_{15}H_{11}NO_3$: C,71.14; H,4.38; N,5.53. Found: C,70.69; H,4.31; N,5.59.

EXAMPLE 3

3-Phenyl-2,1-benzisoxazole-5-acetic acid

A solution of 5.0 g (0.021 mole) of 3-phenyl-2,1-benzisoxazole-5-acetonitrile, 100 ml of ethanol, and 10 ml of 20% sodium hydroxide was heated at reflux under a nitrogen atmosphere for 20 hr. The solution was poured into 800 ml of water, let stand for 0.5 hr and filtered. The filtrate was treated with charcoal, filtered, and the filtrate made acidic with concentrated hydrochloric acid. The mixture was allowed to stand at ambient temperature overnight and then filtered. The filter cake was washed with water, air dried, and recrystallized from 2-propanol to yield 2.9 g (54%) of gray powder, m.p. 173°–174° C. with decomposition.

Analysis: Caculated for $C_{15}H_{11}NO_3$: C,71.14; H,4.38; N,5.53. Found: C,71.16; H,4.33; N,5.57.

EXAMPLE 4

α-Methyl-3-phenyl-2,1-benzisoxazole-5-acetic acid

A mixture of 7.5 g (0.0302 mole) of α-methyl-3-phenyl-2,1-benzisoxazole-5-acetonitrile, 25 ml of 10% sodium hydroxide solution and 160 ml of ethanol was stirred and heated at reflux under an argon atmosphere for 20 hr. The solvents were evaporated under reduced pressure and the residue was partitioned between water (250 ml) and ethyl ether (100 ml). The layers were separated and the aqueous layer was extracted twice with 200 ml portions of ethyl ether. The aqueous layer was treated with charcoal and filtered through Celite. The filtrate pH was adjusted to 2 with concentrated hydrochloric acid. The mixture was extracted with methylene chloride (900 ml) and the organic layer was washed twice with 300 ml portions of water and dried over magnesium sulfate. The solvent was evaporated under reduced pressure to give 4.2 g of a brownish, viscous residue that solidified upon standing. The solid was dissolved in 400 ml of ethyl ether, treated with charcoal and filtered. The filtrate was evaporated under reduced pressure to give a solid. The solid was recrystallized from isopropyl ether-petroleum ether (30°–60° C.) to give 3.6 g (44%) of bright-yellow solid, m.p. 145°–149° C.

Analysis: Calculated for $C_{16}H_{13}NO_3$: C,71.90; H,4.90; N,5.24. Found: C,71.78; H,4.90; N,5.15.

EXAMPLE 5

3-Phenyl-2,1-benzisoxazole-6-acetic acid

A mixture of 2.9 g (0.012 mole) of crude 3-phenyl-2,1-benzisoxazole-6-acetonitrile, 10 ml of 20% sodium hydroxide, and 75 ml of ethanol was heated at reflux under a nitrogen atmosphere overnight. The dark solution was cooled and poured into 600 ml of water. The mixture was filtered through Celite, treated with charcoal and again filtered. The filtrate was made acidic with concentrated hydrochloric acid and a solid precipitated. The solid was collected by filtration, washed with water, dried, and recrystallized from 2-propanol (charcoal) to give 2.1 g (66%) of brown powder, m.p. 162°–177° C., with decomposition.

Analysis: Calculated for $C_{15}H_{11}NO_3$: C,71.14; H,4.38; N,5.53. Found: C,71.16; H,4.45; N,5.57.

EXAMPLE 6

α-Methyl-3-phenyl-2,1-benzisoxazole-6-acetic acid

A mixture of 8.3 g (0.0334 mole) of α-methyl-3-phenyl-2,1-benzisoxazol-6-acetonitrile, 25 ml of 10% sodium hydroxide solution and 160 ml of ethanol was stirred and heated at reflux under an argon atmosphere for 19 hr. The solvents were evaporated under reduced pressure and the dark brown gummy residue was dissolved in 1 liter of water and filtered through Celite. The filtrate was treated with charcoal and filtered through Celite. The filtrate pH was adjusted to 2.1 with concentrated hydrochloric acid and then extracted with five 200 ml portions of methylene chloride. The combined methylene chloride extracts were washed twice with 200 ml portions of water and dried over magnesium sulfate. The solvent was evaporated under reduced pressure to give 2.9 g of solid. The solid was dissolved in ethyl ether, treated with charcoal and filtered. The filtrate was evaporated under reduced pressure to give a solid. The solid was twice recrystallized from ethyl ether-petroleum ether (30°-60° C.) then from isopropyl ether to give 1.8 g (20%) of light yellow solid, m.p. 147.5°-149.5° C.

Analysis: Calculated for $C_{16}H_{13}NO_3$: C,71.90; H,4.90; N,5.24. Found: C,71.60; H,4.89; H,5.18.

EXAMPLE 7

3-Phenyl-2,1-benzisoxazole-7-acetic acid

A mixture of 7.0 g (0.03 mole) of 3-phenyl-2,1-benzisoxazol-7-acetonitrile, 25 ml of 20% sodium hydroxide and 75 ml of 95% ethanol was heated at reflux under nitrogen atmosphere for 17 hr. The mixture was diluted to 500 ml with water, titrated with concentrated hydrochloric acid to pH 7.0 and filtered. The filtrate was treated with charcoal and then acidified. The precipitate was collected and recrystallized from isopropyl alcohol to give 5.0 (66%) of yellow needles, m.p. 180°-183.5° C.

Analysis: Calculated for $C_{15}H_{11}NO_3$: C,71.14; H,4.38; N,5.53. Found: C,71.48; H,4.42; N,5.60.

EXAMPLE 8

α-Methyl-3-phenyl-2,1-benzisoxazole-7-acetic acid

A mixture of 7.7 g (0.031 mole) of α-methyl-3-phenyl-2,1-benzisoxazole-7-acetonitrile, 20 ml of 20% sodium hydroxide and 150 ml of 95% ethanol was heated at reflux and under an argon atmosphere for 21 hr. The reaction mixture was poured into 1.2 liters of water and filtered. The filtrate was treated with charcoal and filtered through Celite. The filtrate pH was adjusted to 7 with concentrated hydrochloric acid and filtered. The filtrate pH was adjusted to 2 with concentrated hydrochloric acid and allowed to stand at ambient temperature. The resulting solid was collected by filtration, air-dried, and recrystallized from cyclohexane-ethyl ether to give 2.6 g (31%) of light-tan solid, m.p. 140°-144° C.

Analysis: Calculated for $C_{16}H_{13}NO_3$: C,71.90; H,4.90; N,5.24. Found: C,71.77; H,4.94; N,5.16.

EXAMPLE 9

3-(4-Fluorophenyl)-2,1-benzisoxazole-7-acetic acid

A mixture of 3.2 g (0.0127 mole) of 3-(4-fluorophenyl)-2,1-benzisoxazole-7-acetonitrile, 10 ml of 20% sodium hydroxide and 150 ml of ethanol was heated at reflux under an argon atmosphere for 4 hr. The solvents were evaporated under reduced pressure and the residue was partitioned between diethyl ether and water (400 ml each). The layers were separated and the aqueous layer was extracted twice with 100 ml portions of diethyl ether. The aqueous layer was treated with charcoal and filtered through Celite. The filtrate was acidified with concentrated hydrochloric acid to pH 2 and let stand in the refrigerator for 60 hr. The resulting solid was collected by filtration, dried, and recrystallized from diethyl ether to give 0.3 g (10%) of light yellow crystals, m.p. 170°-171° C.

Analysis: Calculated for $C_{15}H_{10}FNO$: C,66.42; H,3.72; N,5.16. Found: C,66.13; H,3.80; N,5.11.

EXAMPLE 10

3-(4-Chlorophenyl)-2,1-benzisoxazole-7-acetic acid

A mixture of 3.9 g (0.015 mole) of 3-(4-chlorophenyl)-2,1-benzisoxazol-7-acetonitrile, 10 ml of 20% sodium hydroxide and 75 ml of 95% ethanol was heated at reflux under a nitrogen atmosphere for 17 hr. The mixture was poured into 600 ml of water and filtered. The filtrate was treated with charcoal and filtered through Celite. The filtrate was adjusted to pH 7 with concentrated hydrochloric acid and the mixture filtered. The filtrate was made acidic with concentrated hydrochloric acid and a solid precipitated. The solid was collected by filtration and recrystallized from 2-propanol to yield 1.6 g (38%) of pale-yellow needles, m.p. 200°-202° C. with decomposition.

Analysis: Calculated for $C_{15}H_{10}ClNO_3$: C,62.62; H,3.50; N,4.87. Found: C,62.58; H,3.52; N,4.88.

EXAMPLE 11

3-(4-Bromophenyl)-2,1-benzisoxazole-7-acetic acid

A mixture of 16.0 g (0.0511 mole) of 3-(4-bromophenyl)-2,1-benzisoxazole-7-acetonitrile, 30 ml of 20% sodium hydroxide solution and 250 ml of ethanol was heated at reflux under an argon atmosphere for 4 hr, poured into 1.2 liters of ice water and the insoluble material was removed by filtration. The filtrate was treated with charcoal and filtered. The filtrate pH was adjusted to 2 with concentrated hydrochloric acid and the resulting solid was collected by filtration. The solid was dissolved in acetone, treated with charcoal and filtered. The filtrate was evaporated under reduced pressure to give a solid. The solid was recrystallized from acetone to give 1.7 g (10%) of light-yellow crystals, m.p. 190°-192° C.

Analysis: Calculated for $C_{15}H_{10}BrNO_3$: C,54.24; H,3.04; N,4.22. Found: C,54.59; H,3.05; N,4.19.

EXAMPLE 12

5-Chloro-3-phenyl-2,1-benzisoxazole-7-acetic acid

A mixture of 3.6 g (0.013 mole) of crude 5-chloro-3-phenyl-2,1-benzisoxazole-7-acetonitrile, 150 ml of ethanol and 10 ml of 20% sodium hydroxide was heated at reflux under a nitrogen atmosphere overnight. The dark mixture was concentrated and the residue was diluted with 400 ml of water. The mixture was filtered and the filtrate was treated with charcoal. The mixture was filtered through celite and the filtrate was made acidic with concentrated hydrochloric acid. The resulting solid was collected by filtration, washed with water and recrystallized from 2-propanol. The solid was then recrystallized from ethyl acetate to yield 0.6 g (16%) of yellow powder, m.p. 188°-190° C. with decomposition.

Analysis: Calculated for $C_{15}H_{10}ClNO_3$: C,62.62; H,3.50; N,4.87. Found: C,62.49; H,3.48; N,5.00.

EXAMPLE 13

3-Phenyl-2,1-benzisoxazole-7-acetic acid ethyl ester

To a stirred slurry of 0.7 g (0.014 mole) of washed (petroleum ether), 50% sodium hydride/oil in 5 ml of dry dimethylformamide was added a solution of 2.9 g (0.012 mole) of 3-phenyl-2,1-benzisoxazol-7-acetic acid in 15 ml of dimethylformamide. The mixture was stirred at ambient temperature for 10 minutes and then 2.0 g (0.013 mole) of ethyl iodide was added. The dark solution was stirred at ambient temperature for 1 hr and then poured into 500 ml of water and let stand overnight. The mixture was filtered and the collected solid was recrystallized from 2-propanol to give 0.2 g (6%) of solid, m.p. 97°–98° C.

Analysis: Calculated for $C_{17}H_{15}NO_3$: C,72.58; H,5.38; N,4.98. Found: C,72.80; H,5.34; N,5.01.

EXAMPLE 14

3-Phenyl-2,1-benzisoxazole-7-acetamide

A slurry of 4.0 g (0.017 mole) of 3-phenyl-2,1-benzisoxazol-7-acetonitrile in 175 ml of t-butanol was heated to reflux and treated with 5 g (0.09 mole) of powdered potassium hydroxide. The deep blue colored reaction mixture was heated at reflux for 0.5 hr, cooled and poured into 800 ml of water. The mixture was extracted with three 100 ml portions of methylene chloride. The combined extracts were washed with water, dried over sodium sulfate, and concentrated to give a brown solid as residue. The solid was recrystallized from 2-propanol (charcoal) and then subjected to vacuum sublimation at 160°–170° C. to yield 0.5 g (12%) of an off-white powder, m.p. 191°–192° C. after recrystallization from absolute ethyl alcohol.

Analysis: Calculated for $C_{15}H_{12}N_2O_2$: C,71.42; H,4.80; N,11.10. Found: C,71.31; H,4.77; N,11.18.

EXAMPLE 15

3-(4-Chlorophenyl)-2,1-benzisoxazole-5-acetamide

A solution of 400 mg (0.00125 mole) of 3-(4-chlorobenzoyl)-4-nitrobenzene acetamide in 20 ml of tetrahydrofuran was warmed to 50° C. and treated with 1 g of tin powder and 1 ml of concentrated hydrochloric acid. The mixture was stirred for 1 hr, then filtered. The filtrate was poured into water and the solid was collected and recrystallized from ethanol-isopropanol to give 50 mg (14%) of light-yellow crystals, m.p. 242.0°–43.5° C.

Analysis: Calculated for $C_{15}H_{11}ClN_2O_2$: C,62.84; H,3.87; N,9.77. Found: C,62.65; H,3.88; N,9.75.

EXAMPLE 16

3-(4-Trifluoromethyl)-2,1-benzisoxazole-7-acetic acid

Following the procedure of Example 11, 3-(4-trifluoromethyl)-2,1-benzisoxazole-7-acetonitrile is hydrolyzed in basic alcoholic medium to the sodium salt of the title compound. The mixture is acidified with hydrochloric acid to give the title compound.

EXAMPLE 17

3-(4-Carboxymethylphenyl)-2,1-benzisoxazole-7-acetic acid

Following the procedure of Example 12, 3-(4-cyanomethyl)-2,1-benzisoxazole-7-acetonitrile in ethanol and double the amount of sodium hydroxide is heated at reflux overnight to give a solution of the disodium salt of the title compound. After concentrating and redissolving the sodium salt in water, the title compound is obtained as precipitate by adding hydrochloric acid.

EXAMPLE 18

5-Chloro-N,N-dimethyl-3-phenyl-2,1-benzisoxazole-7-acetamide

The title compound is prepared by reacting the acid chloride of 5-chloro-3-phenyl-2,1-benzisoxazole-7-acetic acid and dimethylamine in an aprotic solvent. The solution is washed with hydrochloric acid and evaporated. The title compound is obtained from the residue by conventional crystallization from alkanolic solution or by chromatography.

EXAMPLE 19

5-Chloro-N-methyl-3-phenyl-2,1-benzisoxazole-7-acetamide

The title compound is prepared by reacting the acid chloride of 5-chloro-3-phenyl-2,1-benzisoxazole-7-acetic acid and excess monomethylamine in a closed container in an aprotic solvent. The unused methylamine is allowed to escape and the solution is washed with hydrochloric acid followed by aqueous base and evaporated. The title compound is obtained by conventional crystallization from alkanolic solution or by chromatography.

EXAMPLE 20

Following the procedure of Example 11, and substituting the following for 3-(4-bromophenyl)-2,1-benzisoxazole-7-acetonitrile:

(a) 3-phenyl-5-methoxy-2,1-benzisoxazole-7-acetonitrile,
(b) 3-(3,4-dimethoxyphenyl)-2,1-benzisoxazole-7-acetonitrile,
(c) 3-(4-methoxyphenyl)-2,1-benzisoxazole-7-acetonitrile,
(d) 3-(4-iodophenyl)-2,1-benzisoxazole-7-acetonitrile,
(e) 3-(4-bromophenyl)-5-chloro-2,1-benzisoxazole-7-acetonitrile,
(f) 3-(4-bromophenyl)-5-fluoro-2,1-benzisoxazole-7-acetonitrile,
(g) 3-(4-fluorophenyl)-5-methyl-2,1-benzisoxazole-7-acetonitrile,
(h) 3-(2,4-dichlorophenyl)-5-methyl-2,1-benzisoxazole-7-acetonitrile,
(i) 3-(4-bromophenyl)-5-methyl-2,1-benzisoxazole-7-acetonitrile,
(j) 3-(4-bromo-2-chlorophenyl)-5-chloro-2,1-benzisoxazole-7-acetonitrile,
(k) 3-(4-bromo-2-chlorophenyl)-2,1-benzisoxazole-7-acetonitrile,
(l) 3-(3,4,5-trimethoxyphenyl)-2,1-benzisoxazole-7-acetonitrile,
(m) 5-chloro-3-(4-methylphenyl)-2,1-benzisoxazole-7-acetonitrile,
(n) 5-chloro-3-[4-(trifluoromethyl)phenyl]-2,1-benzisoxazole-7-acetonitrile, and
(o) 3-(4-chlorophenyl)-5-trifluoromethyl-2,1-benzisoxazole-7-acetonitrile,
there are obtained:
(a) 3-phenyl-5-methoxy-2,1-benzisoxazole-7-acetic acid, (b) 3-(3,4-dimethoxyphenyl)-2,1-benzisoxazole-7-acetic acid,
(c) 3-(4-methoxyphenyl)-2,1-benzisoxazole-7-acetic acid,
(d) 3-(4-iodophenyl)-2,1-benzisoxazole-7-acetic acid,
(e) 3-(4-bromophenyl)-5-chloro-2,1-benzisoxazole-7-acetic acid,
(f) 3-(4-bromophenyl)-5-fluoro-2,1-benzisoxazole-7-acetic acid,
(g) 3-(4-fluorophenyl)-5-methyl-2,1-benzisoxazole-7-acetic acid,
(h) 3-(2,4-dichlorophenyl)-5-methyl-2,1-benzisoxazole-7-acetic acid,
(i) 3-(4-bromophenyl)-5-methyl-2,1-benzisoxazole-7-acetic acid,
(j) 3-(4-bromo-2-chlorophenyl)-5-chloro-2,1-benzisoxazole-7-acetic acid,
(k) 3-(4-bromo-2-chlorophenyl)-2,1-benzisoxazole-7-acetic acid,
(l) 3-(3,4,5-trimethoxyphenyl)-2,1-benzisoxazole-7-acetic acid,
(m) 5-chloro-3-(4-methylphenyl)-2,1-benzisoxazole-7-acetic acid,
(n) 5-chloro-3-[4-(trifluoromethyl)phenyl]-2,1-benzisoxazole-7-acetic acid, and
(o) 3-(4-chlorophenyl)-5-trifluoromethyl-2,1-benzisoxazole-7-acetic acid.

EXAMPLE 21

5-Chloro-7-[2-oxo-2-(1-pyrrolidinyl)ethyl]-3-phenyl-2,1-benzisoxazole

The title compound is prepared by reacting the acid chloride of 5-chloro-3-phenyl-2,1-benzisoxazole-7-acetic acid with pyrrolidine in an aprotic solvent and washing the reaction mixture with sodium bicarbonate and isolating the product by crystallization.

EXAMPLE 22

5-Chloro-7-[2-oxo-2-(1-piperidinyl)ethyl]-3-phenyl-2,1-benzisoxazole

The title compound is prepared by reacting the acid chloride of 5-chloro-3-phenyl-2,1-benzisoxazole-7-acetic acid with piperidine in an aprotic solvent and washing the reaction mixture with sodium bicarbonate solution.

EXAMPLE 23

5-Chloro-7-[2-(4-morpholinyl)-2-oxoethyl]-3-phenyl-2,1-benzisoxazole

The title compound is prepared by reacting the acid chloride of 5-chloro-3-phenyl-2,1-benzisoxazole-7-acetic acid with morpholine in an aprotic solvent and washing the reaction mixture with sodium bicarbonate solution.

EXAMPLE 24

5-Chloro-7-[2-oxo-2-(1-piperazinyl)ethyl]-3-phenyl-2,1-benzisoxazole

The title compound is prepared by reacting the acid chloride of 5-chloro-3-phenyl-2,1-benzisoxazole-7-acetic acid with piperazine in an aprotic solvent and washing the reaction mixture with sodium bicarbonate solution.

EXAMPLE 25

5-Chloro-7-[2-oxo-2-(4-phenyl-1-piperazinyl)ethyl]-3-phenyl-2,1-benzisoxazole

The title compound is prepared by reacting the acid chloride of 5-chloro-3-phenyl-2,1-benzisoxazole-7-acetic acid with N-phenyl-piperazine in an aprotic solvent and washing the reaction mixture with sodium bicarbonate solution.

EXAMPLE 26

7-[2-(4-Acetyl-1-piperazinyl)-2-oxoethyl]-5-chloro-3-phenyl-2,1-benzisoxazole

The title compound is prepared by reacting the acid chloride of 5-chloro-3-phenyl-2,1-benzisoxazole-7-acetic acid with N-acetylpiperazine in an aprotic solvent and washing the reaction mixture with sodium bicarbonate solution.

EXAMPLE 27

5-Chloro-7-[2-(4-hydroxy-4-phenyl-1-piperidinyl)-2-oxoethyl]-3-phenyl-2,1-benzisoxazole The title compound is prepared by reacting the acid chloride of 5-chloro-3-phenyl-2,1-benzisoxazole-7-acetic acid with 4-hydroxy-4-phenyl-piperidine in an aprotic solvent and washing the reaction mixture with sodium bicarbonate solution.

EXAMPLE 28

3-(2,4-Dichlorophenyl)-2,1-benzisoxazole-7-acetic acid

Following the procedure of Example 11, 3-(2,4-dichlorophenyl)-2,1-benzisoxazole-7-acetonitrile is hydrolyzed in basic alcoholic medium to the sodium salt of the title compound. The mixture is acidified with hydrochloric acid to give the title compound.

EXAMPLE 29

5-Chloro-3-(4-chlorophenyl)-2,1-benzisoxazole-7-acetic acid

Following the procedure of Example 11, 5-chloro-3-(4-chlorophenyl)-2,1-benzisoxazole-7-acetonitrile is hydrolyzed in basic alcoholic medium to the sodium salt of the title compound. The mixture is acidified to give the title compound.

PHARMACOLOGY

Acute Anti-inflammatory Test - Evans Blue Carrageenan Pleural Effusion Assay The method is that of Sancilio and Fishman in TOXICOC. APPL. PHARMAC. 26, 575–584 (1973). Fasted Sprague-Dawley male rats weighing between 250–500 g were randomly divided into control and experimental groups of six animals. One hour after oral administration of the compounds, e.g., Formula I compounds, the rats were etherized and 5 ml of a mild irritant solution (0.075% Evans Blue and 0.5% Carrageenan Type 7) was administered intrapleurally. Five hours later, the animals were sacrificed with carbon dioxide, pleural fluids were collected in calibrated centrifuge tubes and measured. Results were expressed as the average percent decrease in volume of pleural fluid from that of the control group. The carrier was 0.5% Tween 80 in distilled water and was also the control article. Compounds of the foregoing examples generally exhibited good activity in the pleural effusion assay at 100 mg/kg except the compound of Example 4 which was only weakly active.

Chronic Anti-inflammatory Test - Adjuvent Induced Arthritis Assay

A modification of the method of Walz et al., J. PHARMAC. EXP. THER. 178, 223-31 (1971) was used. This consisted of a therapeutic rather than a prophylactic dosing regimen.

Female Lewis Wistar rats, weighing between 150 and 235 grams, were used. On day 0 a tattoo was made on each leg at the point where the Achilles tendon enters the gastrocnemius muscle. This served as a reference point for measuring the limb volume, plethysmographically. Several hours later 0.05 ml of a suspension of 1.5% Mycobacterium butyricum in mineral oil was injected into the subplantar surface of the right hind foot. On day 18 the hind limb volumes of both feet were determined. Animals with significant swelling of the uninjected feet were randomized by block design into groups of seven or eight. They were dosed orally five days/week, starting on day 18, with the last dose being given on day 28. Twenty-four hours after the last dose, the edema of the injected and uninjected feet was determined by difference. Results were expressed as milliliter of edema of the injected and uninjected feet.

In this test the compound of Example 10 was found to be as potent as indomethacin.

Formulation and Administration

The present invention also contemplates novel therapeutic compositions containing the compounds of the invention as active ingredients. Effective quantities of any of the foregoing pharmacologically active compounds may be administered to a living animal body in any one of various ways; for example, orally as in capsules or tablets, parenterally in the form of sterile solutions or suspensions, and in some cases intravenously in the form of sterile solutions. In forming the novel compositions of this invention, the active ingredient is incorporated in a suitable carrier, illustratively, a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerine, glucose syrup and the like.

The pharmacologically active compounds may be advantageously employed in a unit dosage of from 0.1 to 250 milligrams or more depending on the size of the animal. For example, a large animal such as a horse may require tablets of 500-1000 milligrams active ingredient. The unit dosage may be given a suitable number of times daily so that the daily dosage may vary from 0.3 to 450 milligrams. Five to 25 milligrams appears optimum per unit dose.

It is only necessary that the active ingredient constitute an effective amount, i.e., such that a suitable effective dosage will be obtained consistent with the dosage form employed. The exact individual dosages as well as daily dosages will, of course, be determined according to standard medical principles under the direction of a physician or veterinarian.

The active agents of the invention may be combined with other pharmacologically active agents, or with buffers, antacids or the like, for administration and the proportion of the agent in the compositions may be varied widely.

The following are examples of compositions formed in accordance with this invention.

1. Capsules

Capsules of 5 mg., 25 mg., and 50 mg. of active ingredient per capsule are prepared. With the higher amounts of active ingredient, adjustment may be made in the amount of lactose.

| Typical blend for encapsulation | Per capsule, mg. |
|---|---|
| Active ingredient | 5.0 |
| Lactose | 296.7 |
| Starch | 129.0 |
| Magnesium stearate | 4.3 |
| Total | 435.0 mg. |

Additional capsule formulations preferably contain a higher dosage of active ingredient and are as follows.

| Ingredients | Per capsule, mg. |
|---|---|
| Active ingredient | 25.0 |
| Lactose | 306.5 |
| Starch | 99.2 |
| Magnesium stearate | 4.3 |
| Total | 435.0 mg. |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredient by adjustment of weight of dicalcium phosphate.

|  |  | Per tablet, mg. |
|---|---|---|
| (1) | Active ingredient | 5.0 |
| (2) | Corn starch | 13.6 |
| (3) | Corn starch (paste) | 3.4 |
| (4) | Lactose | 79.2 |
| (5) | Dicalcium phosphate | 68.0 |
| (6) | calcium stearate | 0.9 |
|  |  | 170.1 mg. |

Uniformly blend 1, 2, 4, and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and pressed.

3. Injectable—2% sterile solutions.

|  | Per cc. |
|---|---|
| Active ingredient | 20 mg. |
| Preservative, e.g., chlorobutanol | 0.5% weight/volume |
| Water for injection | q.s. |

Prepare solution, clarify by filtration, fill into vials, seal and autoclave.

Various modifications and equivalents will be apparent to one skilled in the art and may be made in the compounds, compositions, and methods of the present invention without departing from the spirit or scope thereof, and it is therefore understood that the invention is to be limited only by the scope of the appended claims.

What is claimed is:

1. A compound selected from the group having the formula:

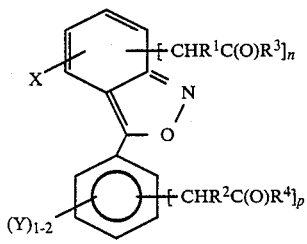

wherein;

R¹ and R² are hydrogen or methyl;

R³ and R⁴ are selected from —OH, loweralkoxy, Am or —OM wherein Am is selected from —NH₂, —NH-loweralkyl, or —N(loweralkyl)₂ and M is a pharmaceutically acceptable cation;

X is selected from hydrogen, halogen, loweralkyl, or nitro;

n and p are zero or one with the proviso that either n or p must be one or both n and p are one; and Y is selected from hydrogen, halogen, loweralkyl, loweralkoxy, nitro or trifluoromethyl with the further proviso that X and/or Y can be loweralkyl when only the 7-position of the benzisoxazole ring is substituted by a —CHR¹C(O)R³ radical and the phenyl radical carries only a Y radical.

2. The compound of claim 1 which is 3-(2,1-benzisoxazol-3-yl)benzeneacetic acid or a pharmaceutically acceptable metal salt thereof.

3. The compound of claim 1 which is 4-(2,1-benzisoxazol-3-yl)benzeneacetic acid or a pharmaceutically acceptable metal salt thereof.

4. The compound of claim 1 which is 3-phenyl-2,1-benzisoxazole-5-acetic acid or a pharmaceutically acceptable metal salt thereof.

5. The compound of claim 1 which is α-methyl-3-phenyl-2,1-benzisoxazole-5-acetic acid or a pharmaceutically acceptable metal salt thereof.

6. The compound of claim 1 which is 3-phenyl-2,1-benzisoxazole-6-acetic acid or a pharmaceutically acceptable metal salt thereof.

7. The compound of claim 1 which is α-methyl-3-phenyl-2,1-benzisoxazole-6-acetic acid or a pharmaceutically acceptable metal salt thereof.

8. The compound of claim 1 which is 3-phenyl-2,1-benzisoxazole-7-acetic acid or a pharmaceutically acceptable metal salt thereof.

9. The compound of claim 1 which is α-methyl-3-phenyl-2,1-benzisoxazole-7-acetic acid or a pharmaceutically acceptable metal salt thereof.

10. The compound of claim 1 which is 3-(4-fluorophenyl)-2,1-benzisoxazole-7-acetic acid or a pharmaceutically acceptable metal salt thereof.

11. The compound of claim 1 which is 3-(4-chlorophenyl)-2,1-benzisoxazole-7-acetic acid or a pharmaceutically acceptable metal salt thereof.

12. The compound of claim 1 which is 3-(4-bromophenyl)-2,1-benzisoxazole-7-acetic acid or a pharmaceutically acceptable metal salt thereof.

13. The compound of claim 1 which is 5-chloro-3-phenyl-2,1-benzisoxazole-7-acetic acid or a pharmaceutically acceptable metal salt thereof.

14. The compound of claim 1 which is 3-phenyl-2,1-benzisoxazole-7-acetic acid ethyl ester.

15. The compound of claim 1 which is 3-phenyl-2,1-benzisoxazole-7-acetamide.

16. The compound of claim 1 which is 3-(4-chlorophenyl)-2,1-benzisoxazole-5-acetamide.

17. A compound selected from the group having the formula:

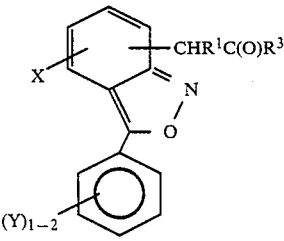

wherein;

R¹ is hydrogen or methyl;

R³ is selected from OH, loweralkoxy, Am or —OM wherein Am is selected from —NH₂, —NH-loweralkyl, or —N(loweralkyl)₂ and M is a pharmaceutically acceptable cation;

X is selected from hydrogen, halogen, loweralkyl, or nitro; and

Y is selected from hydrogen, halogen, loweralkyl, loweralkoxy, nitro or trifluoromethyl with the proviso that X and/or Y can be loweralkyl when only the —CHR¹C(O)R³ radical is in the 7-position.

18. A compound selected from the group having the formula:

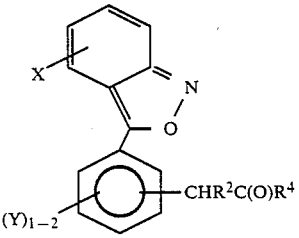

wherein;

R² is hydrogen or methyl;

R⁴ is selected from OH, loweralkoxy, Am or —OM wherein Am is selected from —NH₂, —NH-loweralkyl, or —N(loweralkyl)₂ and M is a pharmaceutically acceptable cation;

X is selected from hydrogen, halogen, or nitro; and

Y is selected from hydrogen, halogen, loweralkoxy, nitro or trifluoromethyl.

19. A method of treating inflammation in a living animal which comprises administering to said animal a therapeutically effective amount of a compound selected from the group having the formula:

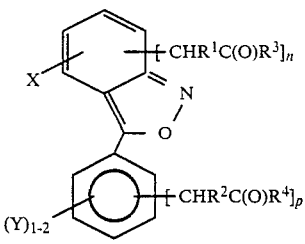

wherein;

R$^1$ and R$^2$ are hydrogen or methyl;

R$^3$ and R$^4$ are selected from OH, loweralkoxy, Am or —OM wherein Am is selected from —NH$_2$, —NH-loweralkyl, or —N(loweralkyl)$_2$ and M is a pharmaceutically acceptable cation;

X is selected from hydrogen, halogen, loweralkyl, or nitro;

n and p are zero or one with the proviso that either n or p must be one or both n and p are one; and Y is selected from hydrogen, halogen, loweralkyl, loweralkoxy, nitro or trifluoromethyl with the further proviso that X and/or Y can be loweralkyl when only the 7-position of the benzisoxazole ring is substituted by a

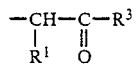

radical and the phenyl radical carries only a Y radical.

20. The method of claim 19 wherein the compound used is 3-(2,1-benzisoxazol-3-yl)benzeneacetic acid or a pharmaceutically acceptable metal salt thereof.

21. The method of claim 19 wherein the compound used is 4-(2,1-benzisoxazol-3-yl)benzeneacetic acid or a pharmaceutically acceptable metal salt thereof.

22. The method of claim 19 wherein the compound used is 3-phenyl-2,1-benzisoxazole-5-acetic acid or a pharmaceutically acceptable metal salt thereof.

23. The method of claim 19 wherein the compound used is α-methyl-3-phenyl-2,1-benzisoxazole-5-acetic acid or a pharmaceutically acceptable metal salt thereof.

24. The method of claim 19 wherein the compound used is 3-phenyl-2,1-benzisoxazole-6-acetic acid or a pharmaceutically acceptable metal salt thereof.

25. The method of claim 19 wherein the compound used is α-methyl-3-phenyl-2,1-benzisoxazole-6-acetic acid or a pharmaceutically acceptable metal salt thereof.

26. The method of claim 19 wherein the compound used is 3-phenyl-2,1-benzisoxazole-7-acetic acid or a pharmaceutically acceptable metal salt thereof.

27. The method of claim 19 wherein the compound used is α-methyl-3-phenyl-2,1-benzisoxazole-7-acetic acid or a pharmaceutically acceptable metal salt thereof.

28. The method of claim 19 wherein the compound used is 3-(4-fluorophenyl)-2,1-benzisoxazole-7-acetic acid or a pharmaceutically acceptable salt thereof.

29. The method of claim 19 wherein the compound used is 3-(4-chlorophenyl)-2,1-benzisoxazole-7-acetic acid or a pharmaceutically acceptable metal salt thereof.

30. The method of claim 19 wherein the compound used is 3-(4-bromophenyl)-2,1-benzisoxazole-7-acetic acid or a pharmaceutically acceptable metal salt thereof.

31. The method of claim 19 wherein the compound used is 5-chloro-3-phenyl-2,1-benzisoxazole-7-acetic acid or a pharmaceutically acceptable metal salt thereof.

32. The method of claim 19 wherein the compound used is 3-phenyl-2,1-benzisoxazole-7-acetic acid ethyl ester.

33. The method of claim 19 wherein the compound used is 3-phenyl-2,1-benzisoxazole-7-acetamide.

34. The method of claim 19 wherein the compound used is 3-(4-chlorophenyl)-2,1-benzisoxazole-5-acetamide.

35. A pharmaceutical composition comprising (a) an acetic acid derivative of 3-aryl-2,1-benzisoxazole compound selected from the group having the formula:

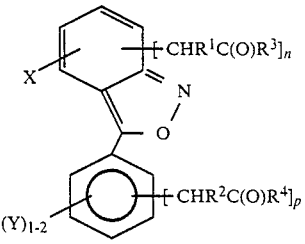

wherein;

R$^1$ and R$^2$ are selected from hydrogen or methyl;

R$^3$ and R$^4$ are selected from —OH, loweralkoxy, Am or —OM wherein Am is selected from —NH$_2$, —NH-loweralkyl, or —N(loweralkyl)$_2$ and M is a pharmaceutically acceptable metal cation;

X is selected from hydrogen, halogen, loweralkyl, or nitro;

n and p are zero or one with the proviso that either n or p must be one or both n and p are one; and Y is selected from hydrogen, halogen, loweralkyl, loweralkoxy, nitro or trifluoromethyl with the further proviso that X and/or Y can be loweralkyl when only the 7-position of the benzisoxazole ring is substituted by a —CHR$^1$C(O)R$^3$ radical and the phenyl radical carries only a Y radical; and (b) a pharmaceutical carrier therefor.

36. The composition of claim 35 wherein the compound is 3-(2,1-benzisoxazol-3-yl)benzeneacetic acid or a pharmaceutically acceptable metal salt thereof.

37. The composition of claim 35 wherein the compound is 4-(2,1-benzisoxazol-3-yl)benzeneacetic acid or a pharmaceutically acceptable metal salt thereof.

38. The composition of claim 35 wherein the compound is 3-phenyl-2,1-benzisoxazole-5-acetic acid or a pharmaceutically acceptable metal salt thereof.

39. The composition of claim 35 wherein the compound is α-methyl-3-phenyl-2,1-benzisoxazole-5-acetic acid or a pharmaceutically acceptable metal salt thereof.

40. The composition of claim 35 wherein the compound is 3-phenyl-2,1-benzisoxazole-6-acetic acid.

41. The composition of claim 35 wherein the compound is α-methyl-3-phenyl-2,1-benzisoxazole-6-acetic acid.

42. The composition of claim 35 wherein the compound is 3-phenyl-2,1-benzisoxazole-7-acetic acid.

43. The composition of claim 35 wherein the compound is α-methyl-3-phenyl-2,1-benzisoxazole-7-acetic acid.

44. The composition of claim 35 wherein the compound is 3-(4-fluorophenyl)-2,1-benzisoxazole-7-acetic acid.

45. The composition of claim 35 wherein the compound is 3-(4-chlorophenyl)-2,1-benzisoxazole-7-acetic acid.

46. The composition of claim 35 wherein the compound is 3-(4-bromophenyl)-2,1-benzisoxazole-7-acetic acid.

47. The composition of claim 35 wherein the compound is 5-chloro-3-phenyl-2,1-benzisoxazole-7-acetic acid.

48. The composition of claim 35 wherein the compound is 3-phenyl-2,1-benzisoxazole-7-acetic acid ethyl ester.

49. The composition of claim 35 wherein the compound is 3-phenyl-2,1-benzisoxazole-7-acetamide.

50. The composition of claim 35 wherein the compound is 3-(4-chlorophenyl)-2,1-benzisoxazole-5-acetamide.

51. A compound selected from the group having the formula:

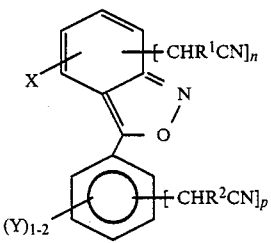

wherein;
$R^1$ and $R^2$ are hydrogen or methyl;
X is hydrogen, halogen, loweralkyl or nitro;
n and p are zero or one with the proviso that either n or p must be one or both n and p are one; and
Y is hydrogen, halogen, loweralkyl, loweralkoxy, nitro or trifluoromethyl with the further proviso that X and/or Y can be loweralkyl when only the 7-position of the benzisoxazole ring is substituted by a

radical and the phenyl radical carries only a Y radical.

52. The compound of claim 51 which is 3-(2,1-benzisoxazol-3-yl)benzeneacetonitrile.

53. The compound of claim 51 which is 4-(2,1-benzisoxazol-3-yl)benzeneacetonitrile.

54. The compound of claim 51 which is 3-phenyl-2,1-benzisoxazole-5-acetonitrile.

55. The compound of claim 51 which is α-methyl-3-phenyl-2,1-benzisoxazole-5-acetonitrile.

56. The compound of claim 51 which is 3-phenyl-2,1-benzisoxazole-6-acetonitrile.

57. The compound of claim 51 which is α-methyl-3-phenyl-2,1-benzisoxazole-6-acetonitrile.

58. The compound of claim 51 which is 3-phenyl-2,1-benzisoxazole-7-acetonitrile.

59. The compound of claim 51 which is α-methyl-3-phenyl-2,1-benzisoxazole-7-acetonitrile.

60. The compound of claim 51 which is 3-(4-fluorophenyl)-2,1-benzisoxazole-7-acetonitrile.

61. The compound of claim 51 which is 3-(4-chlorophenyl)-2,1-benzisoxazole-7-acetonitrile.

62. The compound of claim 51 which is 3-(4-bromophenyl)-2,1-benzisoxazole-7-acetonitrile.

63. The compound of claim 51 which is 3-(2,4-dichlorophenyl)-2,1-benzisoxazole-7-acetonitrile.

64. The compound of claim 51 which is 5-chloro-3-phenyl-2,1-benzisoxazole-7-acetonitrile.

65. The compound of claim 51 which is 5-chloro-3-(4-chlorophenyl)-2,1-benzisoxazole-7-acetonitrile.

66. The compound of claim 51 which is 3-(4-bromophenyl)-5-chloro-2,1-benzisoxazole-7-acetonitrile.

* * * * *